(12) United States Patent
Kennedy et al.

(10) Patent No.: US 10,280,130 B2
(45) Date of Patent: May 7, 2019

(54) POLYISOBUTYLENE-BASED THERMOPLASTIC ELASTOMERS

(71) Applicant: THE UNIVERSITY OF AKRON, Akron, OH (US)

(72) Inventors: Joseph P. Kennedy, Akron, OH (US); Turgut Nugay, Istanbul (TR); Nihan Nugay, Istanbul (TR)

(73) Assignee: THE UNIVERSITY OF AKRON, Akron, OH (US)

( * ) Notice: Subject to any disclaimer, the term of this patent is extended or adjusted under 35 U.S.C. 154(b) by 84 days.

(21) Appl. No.: 15/590,431

(22) Filed: May 9, 2017

(65) Prior Publication Data
US 2017/0240493 A1    Aug. 24, 2017

Related U.S. Application Data

(62) Division of application No. 14/420,464, filed as application No. PCT/US2013/054111 on Aug. 8, 2013.

(60) Provisional application No. 61/681,869, filed on Aug. 10, 2012.

(51) Int. Cl.
| | |
|---|---|
| *C08J 3/28* | (2006.01) |
| *C08F 212/08* | (2006.01) |
| *C08F 255/10* | (2006.01) |
| *C07C 29/58* | (2006.01) |
| *C07C 29/72* | (2006.01) |
| *C07C 41/09* | (2006.01) |
| *C07C 43/166* | (2006.01) |

(52) U.S. Cl.
CPC .............. *C07C 29/72* (2013.01); *C07C 29/58* (2013.01); *C07C 41/09* (2013.01); *C07C 43/166* (2013.01); *C08F 212/08* (2013.01); *C08F 255/10* (2013.01); *C08J 3/28* (2013.01); *C08J 2351/06* (2013.01)

(58) Field of Classification Search
None
See application file for complete search history.

(56) References Cited

U.S. PATENT DOCUMENTS

| | | | | |
|---|---|---|---|---|
| 3,894,119 A | * | 7/1975 | Forbes | C08G 81/021 525/241 |
| 4,758,631 A | * | 7/1988 | Kennedy | C08F 10/10 525/245 |
| 5,084,522 A | | 1/1992 | Frechet | |
| 5,362,814 A | * | 11/1994 | Machida | C08F 290/044 524/504 |
| 5,459,174 A | | 10/1995 | Merrill et al. | |
| 6,011,120 A | * | 1/2000 | Frechet | C08F 8/42 522/148 |
| 6,100,331 A | * | 8/2000 | Teshima | C08F 290/044 525/241 |
| 2003/0065095 A1 | | 4/2003 | Kaneko | |
| 2003/0065098 A1 | | 4/2003 | Puskas | |
| 2009/0227703 A1 | * | 9/2009 | Puskas | A61L 27/34 523/113 |
| 2010/0059452 A1 | * | 3/2010 | Kaszas | C08F 6/003 210/726 |
| 2010/0249316 A1 | | 9/2010 | Kaszas et al. | |

FOREIGN PATENT DOCUMENTS

| | | | | |
|---|---|---|---|---|
| EP | 2495262 | | 9/2012 | |
| JP | 2003026895 A | * | 1/2003 | |
| WO | 02096967 A1 | | 12/2002 | |
| WO | WO-2011127562 A1 | * | 10/2011 | ............. A61L 31/10 |

OTHER PUBLICATIONS

Gauthier, "Arborescent Polymers and Other Dendrigraft Polymers: A Journey Into Structural Diversity", Journal of Polymer Science: Part A: Polymer Chemistry, 2007, 3803-3810. (Year: 2007).*
Puskas et al., "Novel Thermoplastic Elastomers Based on Arborescent (Dendritic) Polyisobutylene with Short Copolymer End Sequences", Journal of Polymer Science, Part A: Polymer Chemistry (2009), 47(4), 1148-1158. (Year: 2009).*
Paulo, et al.; (Synthesis of Hyperbranched Polyisobutylenes by Inimer-Type Living Polymerization. 1. Investigation of the Effect of Reaction Conditions, Macromolecules, Jan. 2001, vol. 34, No. 4, pp. 734-739).

* cited by examiner

*Primary Examiner* — Nicole M. Buie-Hatcher
(74) *Attorney, Agent, or Firm* — Renner Kenner Greive Bobak Taylor & Weber

(57) ABSTRACT

The present invention is directed to a new class of thermoplastic elastomers (TPEs) and processes for making them. In some embodiments of the present invention, the end groups of the multi-arm PIB copolymer is a conjugated diene, whereas the other component is a multi-functional dienophile. The components of the TPE of the present invention are chemically connected via the well-known Diels-Alder reaction which is thermally reversible (by the retro-Diels-Alder reaction) at moderately elevated temperatures. The reversibility of the Diels-Alder retro-Diels-Alder reactions allows the recovery of the original components of the TPE and thus its recyclability and also gives the TPE the ability to be reshaped or reformed.

14 Claims, 12 Drawing Sheets

POLYISOBUTYLENE-BASED THERMOPLASTIC ELASTOMERS

CROSS REFERENCE TO RELATED APPLICATIONS

This application is a divisional of U.S. patent application Ser. No. 14/420,464 filed Feb. 9, 2015, which is a national phase filing of International Patent application serial number PCT/US13/54111 filed Aug. 8, 2013, expired, which claims the benefit of U.S. Provisional Patent Application Ser. No. 61/681,869 filed Aug. 10, 2012, the disclosures of each of which are incorporated herein by reference in their entirety.

FIELD OF THE INVENTION

The present invention relates to block copolymers. More particularly, this invention is directed to a new class of thermoplastic elastomers (TPEs) having suitable molecular weight rubbery star- and/or graft-polymers with diene end groups crosslinked with di- or multi-dienophiles under moderately elevated temperatures using Diels-Alder-retro Diels-Alder (DA-rDA) chemistry.

BACKGROUND OF THE INVENTION

TPEs are block co-polymers made of a hard component and a soft component. The two components undergo microphase separation. The solid domains formed by the hard component are glassy or crystalline. The solid domains are dispersed within a matrix of the soft component and act as both physical crosslinkers and filler particles. The polymer chains of the soft component have a $T_g$ below the service temperature and are able to stretch but are restricted from flowing. In the absence of the hard component, the soft component can flow.

TPEs made from copolymers of polyisobutylene (PIB) are well known in the art. See e.g. U.S. Pat. Nos. RE 34,640, 5,633,234, U.S. Pat. Nos. 4,946,899, 5,428,111, 5,458,796, 5,721,331 4,910,261, 6,747,098, and 5,081,179, the disclosures of which are incorporated herein by reference in their entirety. The great advantages of many recent TPE PIB networks over prior PIB networks, such as the well-known general purpose Butyl Rubber, are that (a) they can be made by "liquid rubber" technology (i.e., by mixing two relatively low molecular weight viscous liquid prepolymers in a mold to give a crosslinked rubber), and (b) they can be recycled upon heating ("green liquid rubbers"). Butyl rubber networks, by contrast, are made by first laboriously mixing the high molecular weight uncured rubber with sulfur and various harsh curatives on large steel blenders/mills that require huge amounts of energy to operate; and then cross-linking ("curing") the blend to permanent networks by again heating to high temperatures and pressures. Thus, butyl rubber is a thermoset, i.e., it cannot be recycled. In contrast, TPE can be recycled, and can be prepared by liquid processing technologies, which are far simpler and consume far less energy than conventional methods

SUMMARY OF THE INVENTION

The present invention is directed to a new class of thermoplastic elastomers (TPEs) and processes for making them. The networks are essentially of polyisobutylene (PIB) and are designed for biocompatible medical devices and industrial rubber objects where chemical stability is essential.

In some embodiments of the present invention, the end groups of the multi-arm PIB copolymer is a conjugated diene, whereas the other component is a multi-functional dienophile. Thus, the components of the TPE of the present invention are chemically connected via the well-known Diels-Alder reaction:

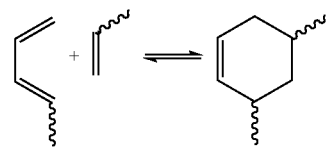

Importantly, the Diels-Alder reaction is thermally reversible (by the retro-Diels-Alder reaction) at moderately elevated temperatures. The reversibility of the Diels-Alder retro-Diels-Alder reactions allows the recovery of the original components of the TPE and thus its recyclability.

In some embodiments, the present invention is directed to a 3-(2-methoxyisopropyl)styrene composition having the formula (i):

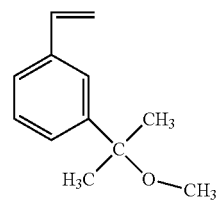

(i)

In some embodiments, the present invention is directed to a method for synthesizing a 3-(2-methoxyisopropyl)styrene composition comprising: (a) reacting a 3-bromostyrene with magnesium to form a compound having the structure of formula (ii):

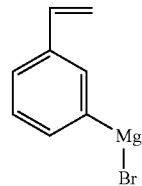

(ii)

(b) reacting the compound of formula (ii) with acetone to form a compound having the structure of formula (iii):

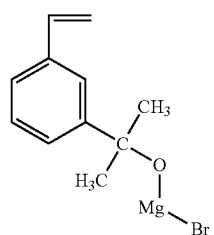

(iii)

(c) reacting the compound of formula (iii) with $H_2O$ to form a compound having the structure of formula (iv); and

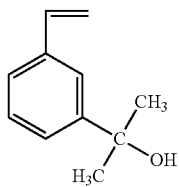

(d) reacting the compound of formula (iv) with CH₃I to form 3-(2-methoxyisproyl) styrene.

In some embodiments, the present invention is directed to a multi-arm polyisobutylene (PIB) polymer comprising: an oligomeric styrene pre-polymer having a sec-butyl head group, a poly(α-methylstyrene) segment from about 3 to about 5 units in length and a poly[3-(2-methoxyisopropyl) styrene] segment from about 3 units to about 50 units in length and having the structure of formula (v):

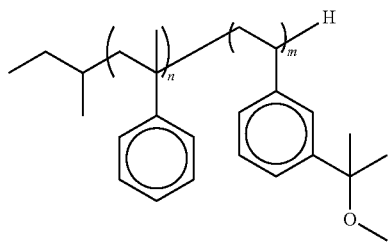

wherein n is an integer from 3 to 5 and m is an integer from 3 to 50; and (b) at least one PIB arm extending from each 3-(2-methoxyisopropyl)styrene wherein said PIB arms are terminated with end groups selected from the group consisting of allyls, dienes, and furans.

In some embodiments, the multi-arm PIB polymer of the present invention may include any of the embodiments described above wherein said end groups are allyl end groups. In some embodiments, the multi-arm PIB polymer of the present invention may include any of the embodiments described above wherein said multi-arm PIB polymer has the structure of formula (vi):

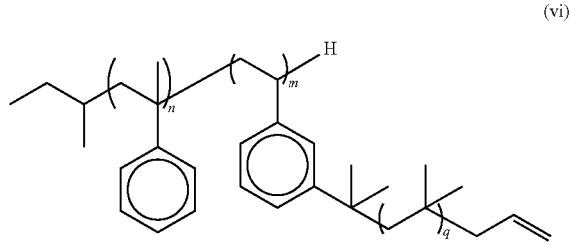

wherein n is an integer from about 3 to about 5, m is an integer from about 3 to about 50, and q is an integer from about 10 to about 10,000.

In some embodiments, the multi-arm PIB polymer of the present invention may include any of the embodiments described above wherein said end groups are diene end groups. In some embodiments, the multi-arm PIB polymer of the present invention may include any of the embodiments described above wherein said end groups are furan end groups.

In some embodiments, the multi-arm PIB polymer of the present invention may include any of the embodiments described above wherein said multi-arm PIB polymer has the structure the formula (vii):

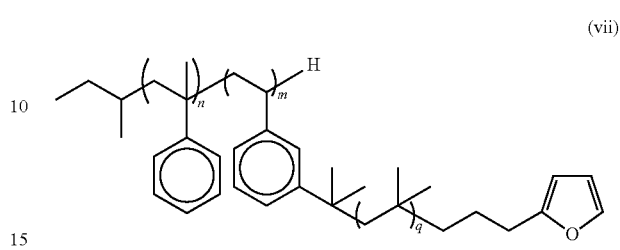

wherein n is an integer from about 2 to about 5, m is an integer from about 3 to about 50, and q is an integer from about 10 to about 10,000.

In some embodiments, the multi-arm PIB polymer of the present invention may include any of the embodiments described above wherein said poly(α-methylstyrene) segment is 4 units in length and said poly[3-(2-methoxyisopropyl)styrene] segment is 6 units in length.

In some embodiments, the multi-arm PIB polymer of the present invention may include any of the embodiments described above wherein said end groups are furan end groups. In some embodiments, the multi-arm PIB polymer of the present invention may include any of the embodiments described above wherein said PIB arms are from about 10 units to about 10,000 units in length.

In some embodiments, the present invention is directed to a method for synthesizing a multi-arm polyisobutylene having an oligomeric styrene, a sec-butyl head group, and allyl end groups comprising: (a) reacting a sec-butyl lithium and an α-methylstyrene to form an α-methylstyrene oligomer of from about 3 units to about 5 units in length, said α-methylstyrene oligomer having a sec-butyl head group and a lithium ion; (b) reacting the an α-methylstyrene oligomer of step (a) with potassium tert-butoxide to replace the lithium ion on the α-methylstyrene oligomer with a potassium ion; (c) reacting the α-methylstyrene oligomer of step (b) with a 3-(2-methoxyisopropyl)styrene to form an oligomeric styrene pre-polymer having a sec-butyl head group, a poly(α-methylstyrene) segment of from about 3 to about 5 units in length, and a poly[3-(2-methoxyisopropyl) styrene] segment of from about 3 to about 50 units in length; (d) combining the oligomeric styrene pre-polymer of step (c), a stoichiometric excess of isobutylene, and a photoinitiator, wherein said isobutylene is added to at least one of the 3-(2-methoxyisopropyl)styrene units of said poly[3-(2-methoxyisopropyl)styrene] segment of said oligomeric styrene pre-polymer by cationic polymerization to create PIB arms of from 10 units to 10,000 units in length extending from each of said 3-(2-methoxyisopropyl)styrene units; and (e) adding allyltrimethylsilane to terminate the isobutylene polymerization and place an allyl group on the end of said PIB arms.

In some other embodiments, the method for synthesizing a multi-arm polyisobutylene having an oligomeric styrene, a sec-butyl head group, and allyl end groups of the present invention may include any of the embodiments described above wherein said poly(α-methylstyrene) segment is 4 units in length and said poly[3-(2-methoxyisopropyl)styrene] segment is 6 units in length.

In some embodiments, the present invention is directed to a method for synthesizing a multi-arm polyisobutylene having an oligomeric styrene, a sec-butyl head group, and diene end groups comprising: (a) dissolving an allyl-terminated multi-arm polyisobutylene and a photoinitiator in a solvent to provide a solution; (b) adding furfuryl mercaptan to provide a solution comprising furfuryl mercaptan and the solution of step (a); (c) irradiating the solution of step (b); and (d) removing the solvent to provide a multi-arm polyisobutylene having an oligomeric styrene, a sec-butyl head group, and diene end groups.

In some embodiments, the method for synthesizing a multi-arm polyisobutylene having an oligomeric styrene, a sec-butyl head group, and diene end groups of the present invention may include any of the embodiments described above further comprising the steps of: (e) redissolving the multi-arm polyisobutylene having an oligomeric styrene, a sec-butyl head group, and a diene end groups of step (d) in hexane; (f) washing the solution of step (e) with methanol; and (g) removing said hexane and said methanol under reduced pressure to leave the multi-arm polyisobutylene having an oligomeric styrene, a sec-butyl head group, and a diene end groups.

In some embodiments, the method for synthesizing a multi-arm polyisobutylene having an oligomeric styrene, a sec-butyl head group, and diene end groups of the present invention may include any of the embodiments described above wherein the photoinitiator is 2,2-dimethoxy-2-phenyl acetophenone and the solvent is dichloromethane.

In some embodiments, the present invention is directed to a thermoplastic elastomer network comprising: (a) a plurality of the multi-arm polyisobutylene having an oligomeric styrene, a sec-butyl head group, and a diene end groups; and (b) a plurality of multi-functional dienophiles, wherein said multi-functional dienophiles are chemically bonded to one or more of said diene end groups to form a thermoplastic elastomer network.

In some embodiments, the thermoplastic elastomer network of the present invention may include any of the embodiments described above and has the formula (viii):

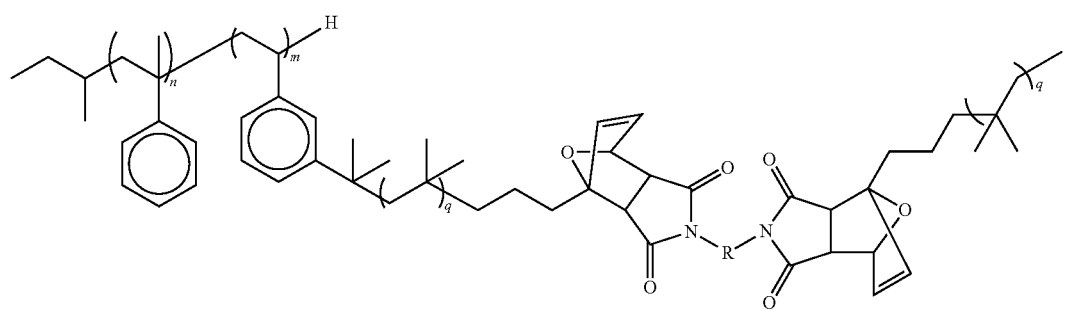

(viii)

wherein n is an integer from about 3 to about 5, m is an integer from about 3 to about 50, q is an integer from about 10 to about 10,000 and R can be either an aliphatic or aromatic group.

In some embodiments, the thermoplastic elastomer network of the present invention may include any of the embodiments described above wherein said diene end group is a furan end group. In some embodiments, the thermoplastic elastomer network of the present invention may include any of the embodiments described above wherein said multi-functional dienophiles are selected from the group consisting of aliphatic/aromatic bis-maleimide, tris-maleimide, and combinations thereof. In some embodiments, the thermoplastic elastomer network of the present invention may include any of the embodiments described above wherein said plurality of multi-functional dienophiles are di-functional dienophiles. In some embodiments, the thermoplastic elastomer network of the present invention may include any of the embodiments described above wherein said plurality of multi-functional dienophiles are bis-maleimide.

In some embodiments, the thermoplastic elastomer network of the present invention may include any of the embodiments described above wherein said plurality of multi-functional dienophiles are tri-functional dienophiles. In some embodiments, the thermoplastic elastomer network of the present invention may include any of the embodiments described above wherein said plurality of multi-functional dienophiles are tris-maleimide. In some embodiments, the thermoplastic elastomer network of the present invention may include any of the embodiments described above further comprising a plurality of multi-functional dienes wherein said multi-functional dienophiles are chemically bonded to one or more of said diene end groups and/or said multi-functional dienes to form a thermoplastic elastomer network. In some embodiments, the thermoplastic elastomer network of the present invention may include any of the embodiments described above wherein the said multi-functional dienes are tris-furan molecules.

In some embodiments, the present invention is directed to a method for making a thermoplastic elastomer network comprising reacting the multi-arm polyisobutylene having an oligomeric styrene, a sec-butyl head group, and a diene end groups with a plurality of multi-functional dienophiles to form a reversibly crosslinked thermoplastic elastomer. In some embodiments, the method for making a thermoplastic elastomer network of the present invention may include any of the embodiments described above wherein said diene end groups are a furan end groups. In some embodiments, the method for making a thermoplastic elastomer network of the present invention may include any of the embodiments described above wherein said multi-functional dienophiles are selected from the group consisting of aliphatic/aromatic bis-maleimide, tris-maleimide, and combinations thereof. In some embodiments, the method for making a thermoplastic elastomer network of the present invention may include any of the embodiments described above wherein said plurality of multi-functional dienophiles are di-functional dienophiles.

In some embodiments, the method for making a thermoplastic elastomer network of the present invention may include any of the embodiments described above wherein said plurality of multi-functional dienophiles are bis-maleimides. In some embodiments, the method for making a thermoplastic elastomer network of the present invention may include any of the embodiments described above wherein said plurality of multi-functional dienophiles are tri-functional dienophiles. In some embodiments, the method for making a thermoplastic elastomer network of the present invention may include any of the embodiments described above wherein said plurality of multi-functional dienophiles are tris-maleimides.

In some embodiments, the present invention is directed to a method for making a thermoplastic elastomer network comprising reacting: the multi-arm polyisobutylene having an oligomeric styrene, a sec-butyl head group, and diene end groups; a plurality of multi-functional dienophiles; and a plurality of tris-furan molecules to form a reversibly cross-linked thermoplastic elastomer.

BRIEF DESCRIPTION OF THE DRAWINGS

For a more complete understanding of the features and advantages of the present invention, reference is now made to the detailed description of the invention along with the accompanying figures in which.

DETAILED DESCRIPTION OF THE ILLUSTRATIVE EMBODIMENTS

The present invention is directed to new thermoplastic elastomers (TPEs) that take advantage of the possibilities offered by Diels-Alder-retro Diels-Alder (DA-rDA) chemistry. The fundamental concept of at least some embodiments of the present invention is to prepare suitable molecular weight rubbery star-and/or graft-polymers with diene end groups and crosslink these readily processible diene-telechelic stars and/or grafts to networks by contacting them, preferably in bulk, with multi-functional dienophiles under moderately elevated temperatures (i.e., in the range of about 50° C. to about 80° C.). Upon heating the networks to somewhat more elevated temperatures (i.e., in the range of about 120-150° C.), the thermally labile DA bonds cleave and the system becomes again processable. Reversible heating and cooling enables the reshaping of the networks, the hallmark of thermoplastic elastomers.

Figure 1:
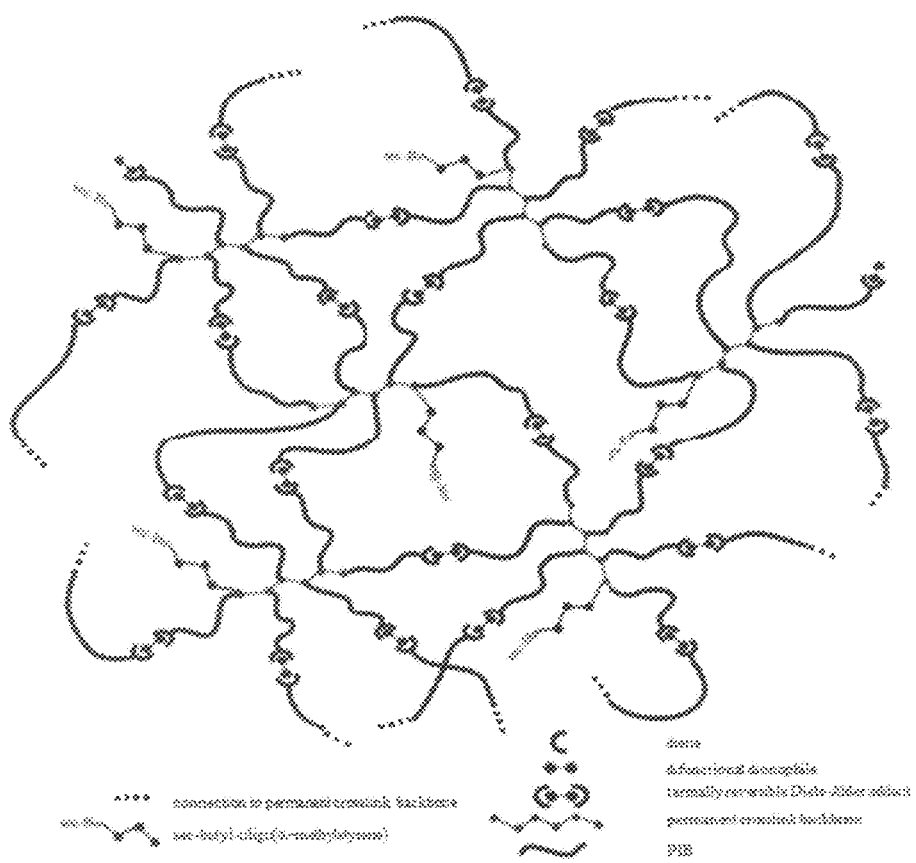
FIG. 1 is a sketch of an idealized PIB Network obtained by a Diels-Alder Reaction, according to at least one embodiment of the present invention.

FIG. 1 is a schematic of a TPE according to some embodiments of the present invention, consisting of a polymer backbone carrying six relatively long polyisobutylene (PIB) arms, each fitted with a diene end group, crosslinked by a difunctional dienophile (FIG. 1). The rubbery (low Tg) PIB arms shown in FIG. 1 provide a strong TPE which is held together by two kinds of crosslinking sites: (a) permanent crosslinks provided by the six-arm graft, and (b) thermally labile crosslinks formed by the DA reaction between the diene end group and the dienophile crosslinker. The latter crosslinks, due to the nature of DA-rDA chemistry, are thermally reversible, i.e., they are stable at moderate temperatures (say at room temperature) but cleave when the network is heated to moderately elevated temperatures (in the range 120-150° C.). As will be appreciated by those of skill in the art, the specific diene/dienophile termini employed will set the use temperature window of the network.

In general arrangement, the basic graft copolymer is a generally star shaped, multi-arm PIB copolymer having a relatively short (generally, about 6-12 mers) polystyrene-derivative backbone comprised of a sec-butyl head group, a poly(α-methylstyrene) oligomer segment and a poly[3-(2-methoxyisopropyl) styrene] oligomer segment, and an plurality of relatively long (about 60 mer, for rubberyness) PIB arms that extend from each mer of the poly[3-(2-methoxyisopropyl)styrene] segment and have a reactive diene end group.

The polystyrene-derivative backbone of some embodiments of the multi-arm PIB copolymer has a short sec-butyl terminated poly(α-methylstyrene) polymer segment of from about 2 mers to about 5 mers in length. In some embodiments, the poly(α-methylstyrene) segment of the polystyrene-derivative backbone is about 4 mers in length. In some embodiments, the sec-butyl terminated poly(α-methylstyrene) polymer segment has the general formula (ix):

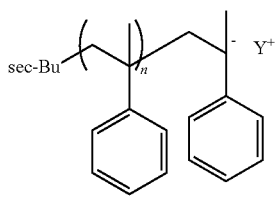

(ix)

wherein n is an integer from about 2 to about 5 and Y is an alkali metal, such as lithium or potassium.

Connected to and extending from the ionized end of the sec-butyl terminated poly(α-methylstyrene) segment is a poly[3-(2-methoxyisopropyl)styrene] polymer segment of from about 3 to about 50 mers in length, to which the PIB arms are attached. The length of the poly[3-(2-methoxyisopropyl)styrene] polymer segment is kept relatively short in order to limit the number of PIB chains on each styrenic backbone. In some embodiments, the poly[3-(2-methoxyisopropyl)styrene] polymer segment is from about 6 mers to about 10 mers in length. In some embodiments, the poly[3-(2-methoxyisopropyl)styrene] polymer segment is from about 6 mers in length.

In some embodiments, the polystyrene-derivative backbone of the graft copolymer has the following formula (v):

(v)

wherein n is an integer from about 2 to about 5 and m is an integer from about 2 to about 50, and is preferably from about 6 to about 10. In some embodiments n is 4 and m is 6. In some embodiments, the polystyrene-derivative backbone of the multi-arm PIB copolymer is a sec-butyl-tetra (α-methylstyrene)-b-hexa [3-(2-methoxyisopropyl) styrene]. As will be discussed in more detail below, sec-butyl terminated polystyrene-derivative backbone of the graft copolymer is used to initiate the polymerization of isobutylene to form the PIB arms of the multi-arm PIB copolymer.

It is believed that the 3-(2-methoxyisopropyl) styrene monomer used to make the poly[3-(2-methoxyisopropyl) styrene] polymer segment of the multi-arm PIB polymer is novel. In some embodiments, the 3-(2-methoxyisopropyl) styrene monomer has the formula (i):

(i)

In some embodiments, the 3-(2-methoxyisopropyl)styrene monomer may be synthesized from 3-bromostyrene through a 3-(2-hydroxyisopropyl) styrene intermediate as set forth in the reaction scheme below.

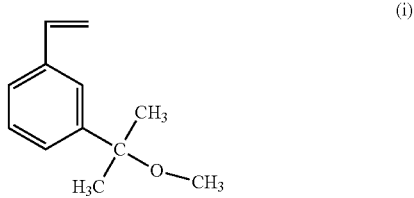

In this embodiment, 3-bromostyrene (x) is dissolved in a suitable solvent. One of ordinary skill in the art will be able to choose an appropriate solvent without undue experimentation. In some embodiments, the solvent is dry THF.

Once dissolved, the 3-bromostyrene (x) is then reacted with magnesium for from about 4 hours to about 6 hours at a temperature of from about −2° C. to about 0° C. under a nitrogen atmosphere to form m-vinyl phenyl magnesium bromide (ii). In some embodiments, the 3-bromostyrene (x) is reacted with magnesium turning in THF at about 15° C. for a period of four hours. Compound (ii) (m-vinyl phenyl magnesium bromide) is then reacted with acetone (xi) to form compound (iii) (m-vinyl phenyl isopropoxy magnesium bromide). In some embodiments, the acetone (xi) is added dropwise over a period of about 30 min at about 0° C., and stirred overnight at about 25° C. The compound (iii) (m-vinyl phenyl isopropoxy magnesium bromide) is then reacted with $H_2O$ to produce 3-(2-hydroxyisopropyl) styrene (iv). In some embodiments, the compound (iii) (m-vinyl phenyl isopropoxy magnesium bromide) is reacted with $H_2O$ in the form of ice and with $NH_4Cl$.

The 3-(2-hydroxyisopropyl) styrene (iv) is then dissolved in a suitable solvent. One of ordinary skill in the art will be able to choose an appropriate solvent without undue experimentation. In some embodiments, the solvent is dry THF. The 3-(2-hydroxyisopropyl) styrene (iv) solution is then added to NaH in THF under a nitrogen atmosphere since NaH gives unwanted vigorous exothermic reaction with atmospheric moisture. The resulting mixture may then be stirred for a period of from about 30 minutes to about 60 minutes at a temperature of from about −5° C. to about 0° C. In some embodiments, mixture may then be stirred for a period of form about 1 hour to about 2 hours. In some embodiments, the mixture may be stirred at a temperature of from about −5° C. to about 0° C. In some embodiments, the mixture may be stirred for about 30 minutes at about 25 C.

The resulting mixture is then reacted with methyl iodide ($CH_3I$) in THF to produce the novel 3-(2methoxyisopropyl) styrene monomer (i). In some embodiments, the methyl iodide ($CH_3I$) is added dropwise to the mixture at a temperature of from about −5° C. to about 0° C. In some embodiments, the temperature may be from about −2° C. to about 0° C. In some embodiments, the temperature may be about 0° C. After the methyl iodide is added to the mixture, the resulting product may be stirred for a period of from 5 hours to 12 hours. In some embodiments, the product may be stirred for about 15 hours.

As one of ordinary skill in the art will appreciate, sodium iodide will be a bi-product of this reaction. The resulting NaI by-product may then be removed by any method known in the art for that purpose. One of ordinary skill in the art will be able to remove the NaI without undue experimentation. In some embodiments, the NaI may be removed by filtration The solvent may likewise be removed by any method known in the art for that purpose. One of ordinary skill in the art will be able to remove the solvent without undue experimentation. In some embodiments, the solvent may be removed by evaporation under reduced pressure.

Figure 2:
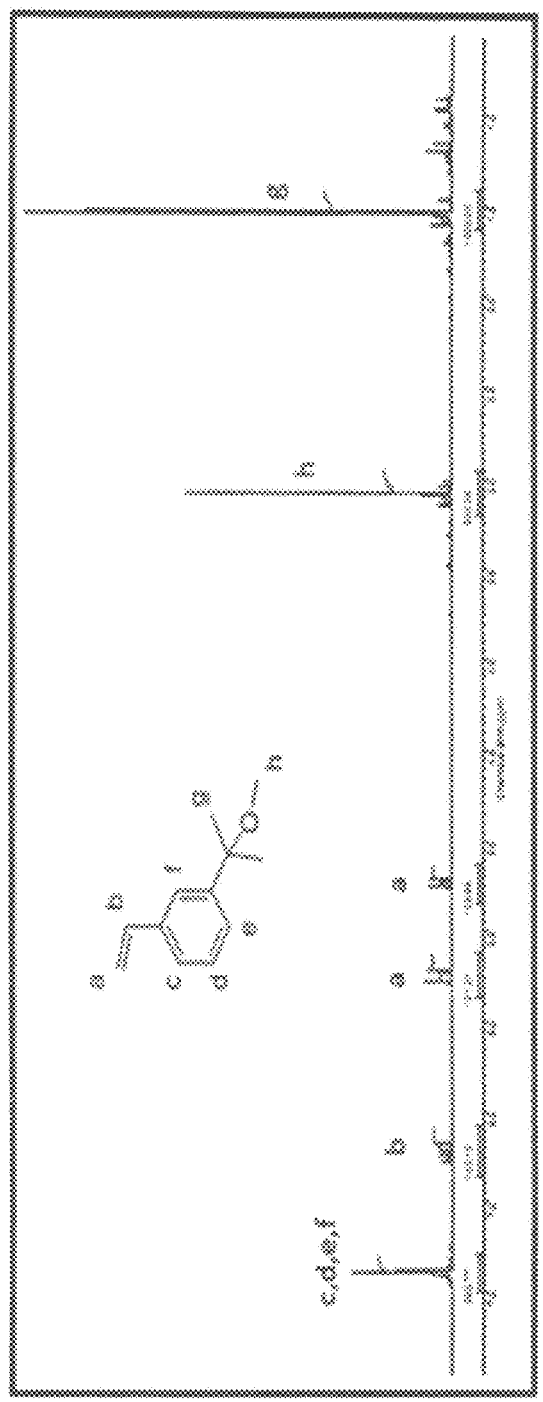
FIG. 2 is a proton nuclear magnetic resonance ($^1$H NMR) spectrum of 3-(2-methoxyisopropyl)styrene according to the method of at least one embodiment of the present invention.

In some embodiments, the novel 3-(2-methoxyisopropyl) styrene monomer (i) may be synthesized as set forth in Example 1 below. A representative $^1H$ NMR spectrum for the novel 3-(2-methoxyisopropyl) styrene monomer is shown in FIG. 2.

The sec-butyl terminated poly(α-methylstyrene) segment of the multi-arm PIB copolymer may be synthesized by any suitable means known in the art and one of ordinary skill in the art will be able to do so without undue experimentation.

In some embodiments, the sec-butyl terminated poly(α-methylstyrene) segment may be synthesized from sec-butyl lithium and α-methylstyrene as set forth below:

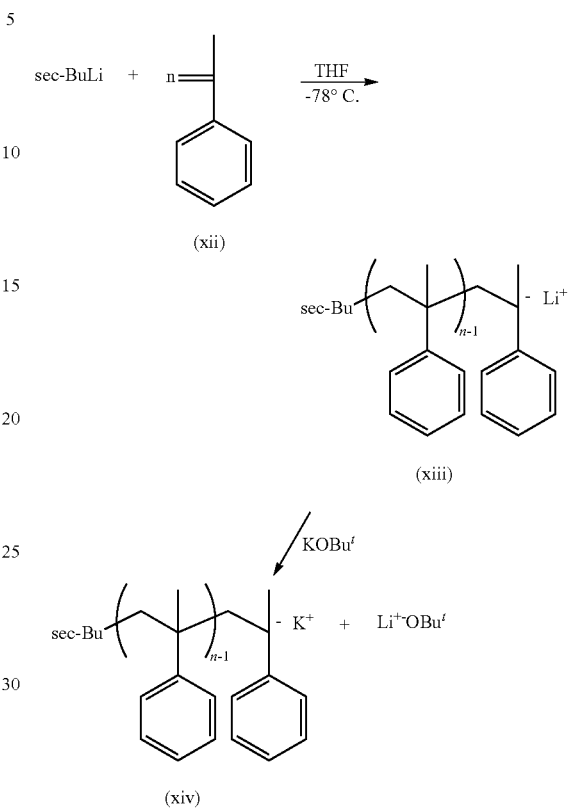

wherein n is an integer from about 2 to about 5.

In some embodiments, the α-methylstyrene monomer may be purified prior to reacting it prior to oligomerization by any means known in the art for that purpose. In some embodiments, the α-methylstyrene monomer may be distilled over calcium hydride and then distilled over dibutlymagnesium or fluorenyllithium under a high vacuum to a separate flask. In some embodiments, the α-methylstyrene monomer may be dissolved in a suitable solvent, such as THF. One of ordinary skill in the art will be able to select a suitable solvent and solubility temperature for the α-methylstyrene monomer without undue experimentation. In some embodiments, the α-methylstyrene monomer may be dissolved in THF at −78° C. Sec-butyllithium may then be added to the α-methylstyrene monomer solution and stirred to form a poly(α-methylstyrene) oligomer with a sec-butyl head group and a lithium ion as shown in formula (xiii). It should be apparent that the poly(α-methylstyrene) oligomer of formula (xiii) is identical to the more general formula (ix) where Y is a lithium ion.

The remainder of the sec-butyl terminated polystyrene-derivative backbone of the multi-arm PIB copolymer may then be synthesized through the addition of the 3-(2-methoxyisopropyl) styrene monomers (i) (described above) to the poly(α-methylstyrene) polymer segment (ix) or (xiv) by any method known in the art for that purpose, to form the poly[3-(2-methoxyisopropyl)styrene] polymer segment of the multi-arm PIB copolymer. The 3-(2-methoxyisopropyl) styrene monomers (i) may be added to the sec-butyl terminated α-methylstyrene segment of the polystyrene-derivative backbone by any suitable means known in the art for that purpose. In some embodiments, the poly(α-methylstyrene) polymer segment (xiii) is reacted with potassium tert-butoxide (KOBu$^t$) to form a poly(α-methylstyrene) polymer segment having a potassium ion (xiv) and a lithium butoxide by-product. The poly(α-methylstyrene) polymer segment having a potassium ion (xiv) is then reacted with the 3-(2-methoxyisopropyl) styrene monomers (i), whereby the 3-(2-methoxyisopropyl) styrene monomers are added to the ionized end of the sec-butyl terminated α-methylstyrene segments, replacing the potassium ion, and oligomerizing from there to form a chain of from 2 to 50 monomer units. Oligomerization will continue until substantially all of the 3-(2-methoxyisopropyl) styrene monomers (i) have reacted or until oligomerization is terminated by any method known in the art for that purpose. The completion of the oligomerization MAY BE confirmed by the $^1$H NMR method. One of ordinary skill in the art will be able to terminate the oligomerization of the 3-(2-methoxyisopropyl) styrene monomers (i) without undue experimentation. In some embodiments, oligomerization of the 3-(2-methoxyisopropyl) styrene monomers (i) may be terminated with the addition of methanol.

In some embodiments, the 3-(2-methoxyisopropyl) syrene monomers may be added to the sec-butyl terminated α-methylstyrene segment of the polystyrene-derivative backbone as set forth below:

cal properties of PIB rubbers and because of the accumulated experience in the art for molecularly engineering the shape, MW, and structural details (end groups) of PIB molecules. In some embodiments, each PIB arm may be from about 10 to about 10,000 mers in length. In some embodiments, each PIB arm may be from about 35 to about 107 mers in length. In some embodiments, each PIB arm may be about 60 mers in length.

For some embodiments of the TPE of the present invention, the number average molecular weight ($M_n$) of the PIB arms is from about 2000 g/mol to about 6000 g/mol. For some embodiments, the number average molecular weight ($M_n$) of the PIB arms is from about 3000 g/mol to about 4000 g/mol. For some embodiments, the number average molecular weight ($M_n$) of the PIB arms is about 3500 g/mol. As one of skill in the art will readily appreciate, the synthesis of a PIB having these molecular weights is readily achievable with living isobutylene polymerization.

This novel multi-arm PIB copolymer can be synthesized from the sec-butyl terminated polystyrene-derivative polymer backbone discussed above by well-established modern methods. In general outline, the novel multi-arm PIB copolymer of the present invention may be made by using the sec-butyl terminated polystyrene-derivative polymer backbone discussed above to initiate the cationic polymerization

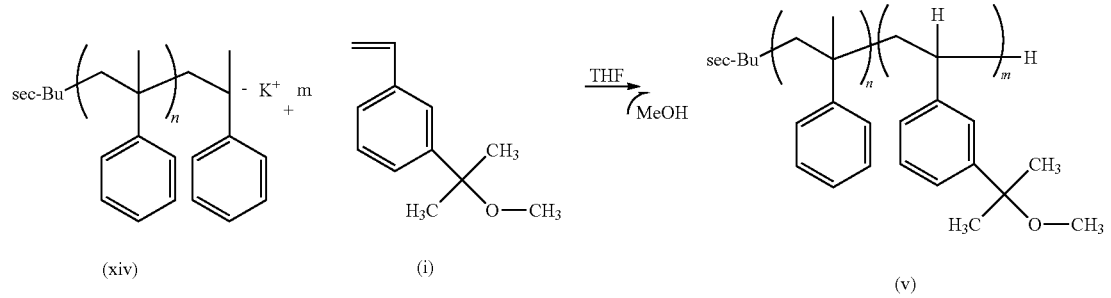

(xiv)   (i)   (v)

wherein n is an integer from about 2 to about 5 and m wherein m is an integer from about 2 to about 50, and is preferably from about 6 to about 10.

As set forth above, the sec-butyl end group, poly(α-methylstyrene) polymer segment, and the poly[3-(2-methoxyisopropyl)styrene] segment together comprise the backbone of the multi-arm PIB copolymer, which is used to initiate the polymerization of isobutylene to form the PIB arms of the copolymer. In some embodiments, the remainder of the sec-butyl terminated polystyrene-derivative backbone of the graft polymer may be synthesized as set forth in Example 2 below.

In some embodiments, the oligomeric 3-(methoxyisopropyl) styrene described above may be prepared by means of an anionic polymerization methodology using cumyl potassium as an initiator. Cumyl potassium is a well known initiator in anionic polymerization. See G. Riess et. al. Macromol Chem., 194, 1411, (1993), the disclosure of which is hereby incorporated by reference in its entirety. In some embodiments, the oligomeric 3-(methoxyisopropyl) styrene segment may be synthesized as set forth in Example 2a below.

Figure 3:
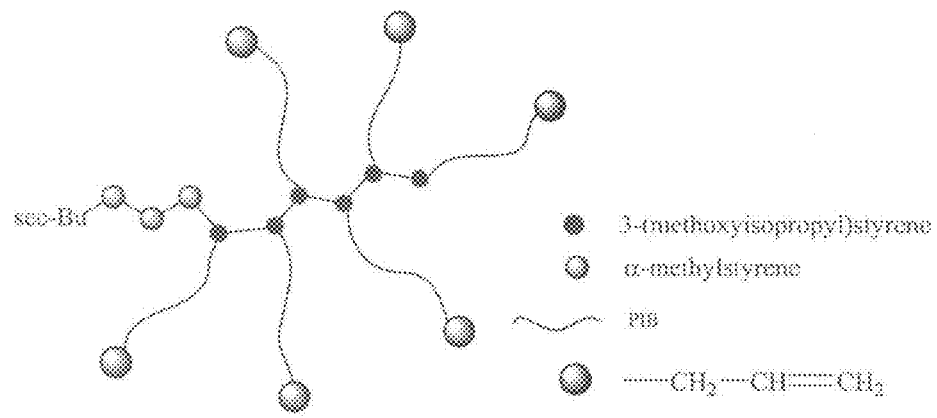
FIG. 3 is a graphical representation of an allyl-terminated multi-arm PIBcopolymer intermediary according to the method of at least one embodiment of the present invention.
Figure 4:
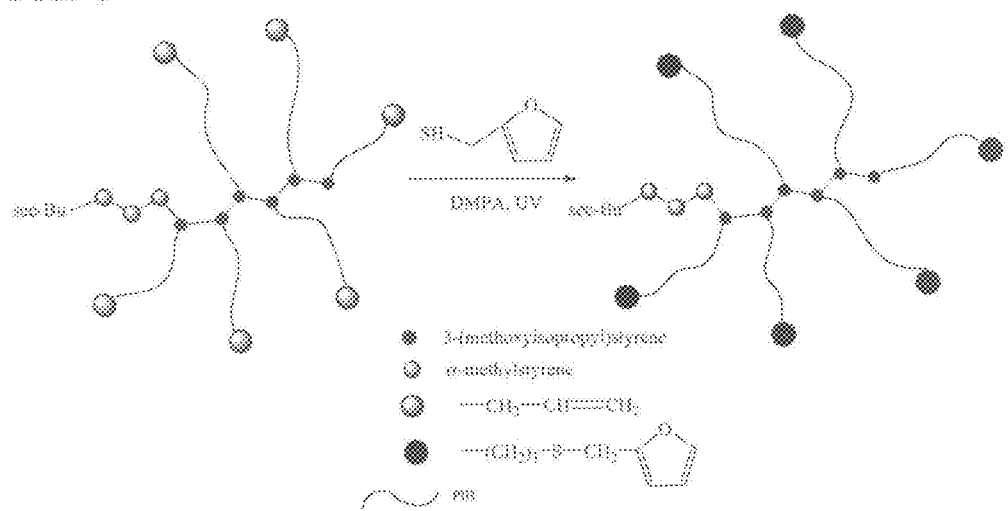
FIG. 4 is a sketch of a reaction mechanism for substituting a diene end group (furan) for the allyl end group of the allyl terminated multi-arm PIBcopolymer intermediary according to the method of at least one embodiment of the present invention.

As set forth above, extending from each one of the 3-(2-methoxyisopropyl) styrene units of the sec-butyl terminated polystyrene-derivative backbone are a plurality of PIB arms. PIB was selected for the arms due to the excellent combination of the physical-mechanical-chemical-biologiof a stoichiometric excess of isobutylene to form the PIB arms of the polymer and then quenching polymerization with an agent such as allyltrimethylsilane (AMS) to form an allyl-terminated multi-arm PIB copolymer intermediary. In some embodiments, the sec-butyl terminated polystyrene-derivative polymer backbone used to initiate the polymerization is sec-butyl-tetra (α-methylstyrene)-β-hexa [3-(2-methoxyisopropyl) styrene]. The allyl-terminated multi-arm PIB copolymer intermediary is shown in FIG. 3. The allyl end groups on the allyl-terminated multi-arm PIB copolymer intermediary are then replaced with a diene end group like furan in a second reaction to form the novel graft polymer of the present invention. The diene-terminated multi-arm PIB copolymer intermediary is shown in FIG. 4.

As those of ordinary skill in the art will recognize, the cationic polymerization of isobutylene should be carried out in/under inert atmosphere conditions and at low temperatures, preferably from about −78° C. to about −90° C., to prevent possible side reactions. In some embodiments, the cationic polymerization of isobutylene takes place under a high vacuum/dry nitrogen system at −80° C. One of ordinary skill in the art will know how to terminate the polymerization of isobutylene into PIB to obtain PIB arms of a desired length. The PIB polymerization may then be quenched using an allyltrimethylsilane, which both terminates the polymerization of isobutylene into PIB and puts an allyl group on the end of the PIB chains to produce the allyl-terminated multi-arm PIB copolymer intermediary (vi). See FIG. 3.

In some embodiments, the allyl-terminated PIB arms are added to the sec-butyl terminated polystyrene-derivative backbone by the following reaction scheme:

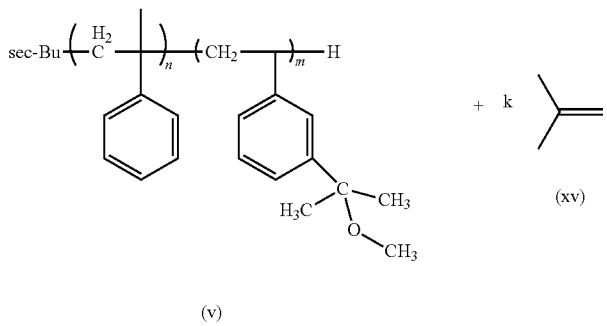

(v)

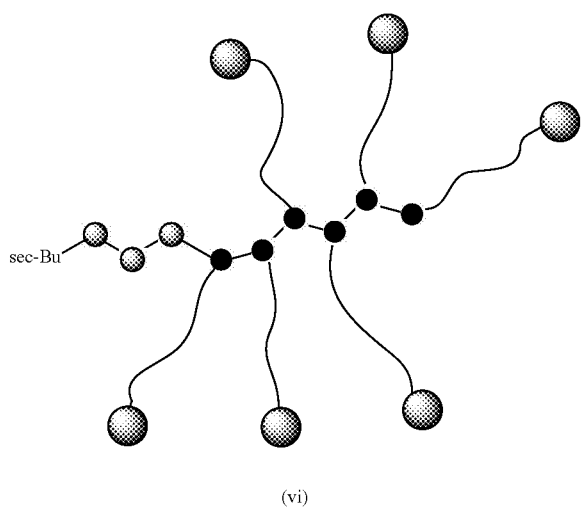

(vi)

● 3-(methoxyisopropyl)styrene

◉ α-methylstyrene

⌇ PIB

◉ —CH₂-CH=CH₂ wherein n is an integer from about 2 to about 5, m wherein m is an integer from about 2 to about 50, and is preferably from about 6 to about 10 and k/m (average number of repeating units in the PIB arms) is from about 35 mers to about 107 mers. In some embodiments, n is 4 and/or m is 6.

Finally, the allyl group on the allyl-terminated multi-arm PIB copolymer intermediary may be replaced by a diene end group to create the novel multi-arm PIB copolymer of the present invention. Suitable diene end groups include, but are not limited to anthracene, fullerene, cyclopentadiene, thiophene, pyrole and their derivatives. The diene end groups may be added using any method known in the art for that purpose. However, as will be apparent to those of skill in the art, the precise mechanism for addition will depend upon the particular diene chosen, among other factors.

In some embodiments, the diene end group is a furan end group and the multi-arm PIB polymer has the formula (vii):

(vii)

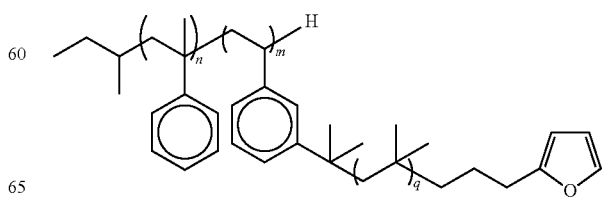

wherein n is an integer from about 2 to about 5, m is an integer from about 3 to about 50, and q is an integer from about 10 to about 10,000. In some embodiments, n is from 3 to 5. In some embodiments, n is 4. In some embodiments, m is from 6 to 10. In some embodiments, m is 6. In some embodiments, q is from 35 to 107. In some embodiments, q is from 50 to 80. In some embodiments, q is 60. In some embodiments, n is from 3 to 5, m is from 6 to 10, and q is from 35 to 107. In some embodiments, n is 4, m is 6, and q is 60.

In some embodiments, the diene end group is a furan end group and may be added to the PIB polymer by the following general procedure. The allyl terminated multi-arm PIB copolymer intermediary discussed above and a photoinitiator such as 2,2-dimethoxy-2-phenyl acetophenone (DMPA) are dissolved in a solvent, such as dichloromethane, under a nitrogen or other inert atmosphere. Other suitable photoinitiators include, but are not limited to benzophenon, 1-hydroxy-cyclohexyl-phenyl-ketone. Other suitable solvents include, but are not limited to toluene, hexane and benzene (good solvents for PIB with low radical transfer constant). In some embodiments, the photoinitiator is DMPA and the solvent is dichloromethane.

After dissolution, furfural mercaptan was added and the solution irradiated using a medium pressure Hg lamp to form the furan-functionalized multi-arm PIB copolymer of at least one some embodiments of the present invention. Any lamp known or unknown which is suitable for the particular photoinitiator chosen may be used. One of ordinary skill in the art will be able to select a suitable lamp for the photoinitiator used.

The solvent may then be removed by any means known in the art for that purpose to produce a crude reaction product comprising the furan-functionalized multi-arm PIB copolymer. One of ordinary skill in the art will know how to remove the solvent without undue experimentation. The crude reaction product comprising the furan-functionalized multi-arm PIB copolymer may be purified. One of ordinary skill in the art will know how to remove the solvent without undue experimentation. The crude reaction mixture may be purified by any means known in the art for that purpose. In some embodiments, the crude reaction product may be purified by redissolving it in an organic solvent such as hexane and washing it in a polar solvent such as methanol.

In some embodiments, a furan end group and may be added to the PIB polymer using the reaction scheme set forth in FIG. 4.

As set forth above, the TPEs of the present invention are cross-linked using Diels-Alder-retro Diels-Alder (DA-rDA) chemistry. Chemical bonds are formed between the diene end groups on the PIB arms of the graft polymer and multi-functional dienophile crosslinkers. These crosslinking compounds are multi-functional in the sense that they have more than one dienophile functional group and can bind to the diene end groups on more than one PIB arm. As these multi-functional dienophile crosslinkers bind to diene end groups from different polymer chains, the polymer is crosslinked and a TPE network formed. (See FIG. 1).

Other suitable dienophile crosslinkers include, but are not limited to aliphatic/aromatic bis-maleimide, tris-maleimide, multi-maleimide.

Figure 5:
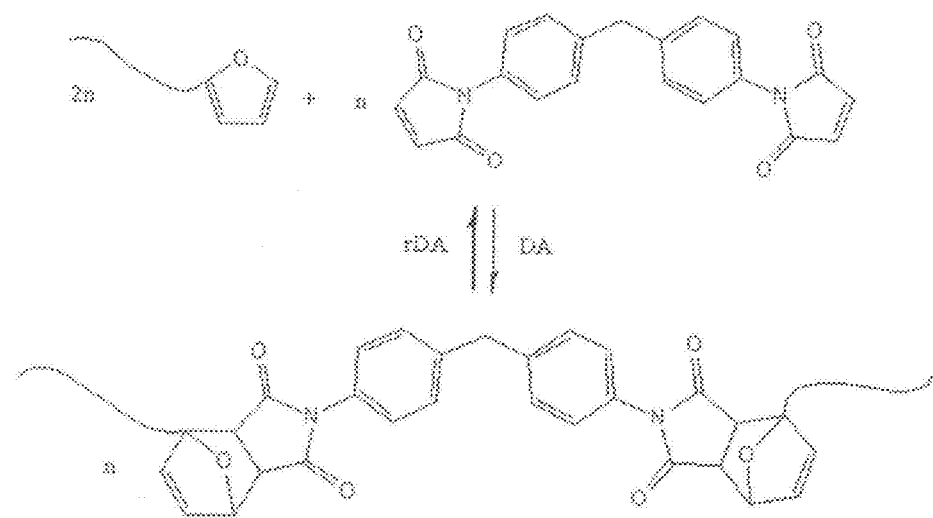
FIG. 5 is a graphic showing the Diels-Alder—reverse Diels-Alder crosslinking reaction according to at least some embodiments of the present invention.

In some embodiments, a furan (F) group was selected as the diene at the end of PIB arms and a di, tri, or multi-bismaleimide (MI) may be used as the dienophile crosslinker. The furan end groups on the multi-arm PIB copolymer and the maleimide end groups react to form crosslinks by a conventional Diels-Alder reaction as shown in FIG. 5. In should be appreciated that the F/MI pair is known to be one of the fastest reacting diene/dienophile pair. See A. Gandini, M. N. Segacem, Progress in Polym. Sci., 22, 1203, (1997) and G. Tillet, Soutevin, S. Ameduri, Progress in Polym. Sci., 36, 191, (2011), the disclosures of which are incorporated herein by reference in their entirety. Other suitable diene/dienophile pairs include, but are not limited to anthracene, fullerene, cyclopentadiene, thiophene, pyrole and their derivatives/aliphatic-aromatic bis-maleimide, tris-maleimide, multi-maleimide.

Upon crosslinking, a number average arm molecular weight $M_n$ of about 3500 g/mol gives an average molecular weight between cross-links ($M_c$) of about 7000 g/mol, which is appropriate for a high quality elastomer. In some embodiments, the TPE has the formula (viii):

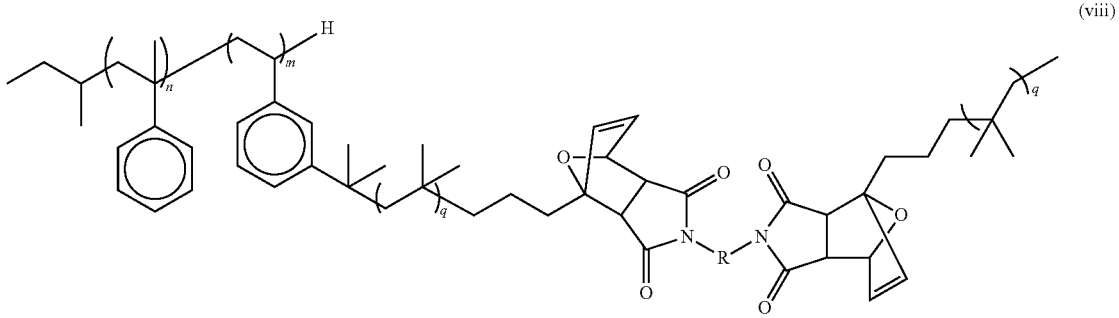

(viii)

wherein n is an integer from about 3 to about 5, m is an integer from about 3 to about 50, q is an integer from about 10 to about 10,000 and R can be either an aliphatic or aromatic group. In some embodiments, n is from 3 to 5. In some embodiments, n is 4. In some embodiments, m is from 6 to 10. In some embodiments, m is 6. In some embodiments, q is from 35 to 107. In some embodiments, q is 60. In some embodiments R may be a butyl, phenylene, or methylene-4,1-phenylene group, or any combination thereof. In some embodiments, n is from 3 to 5, m is from 6 to 10, and q is from 35 to 107. In some embodiments, n is 4, m is 6, and q is 60.

Figure 6:
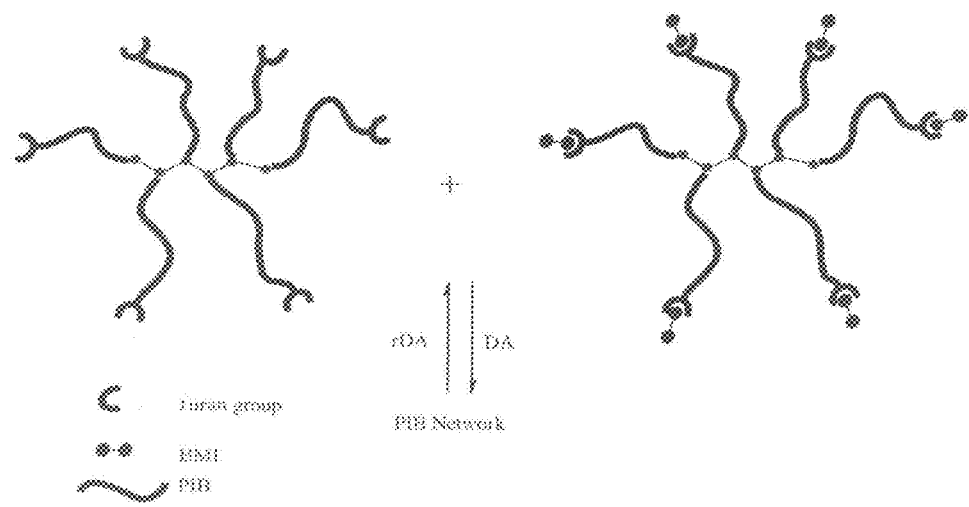
FIG. 6 is sketch showing the reaction of a diene (furan) terminated multi-arm PIB copolymer with multi-functional dienophiles (bis-maleimide) to form a TPE network according to at least one embodiment of the present invention.

In some embodiments, the TPE may be formed as shown in FIGS. 5 and 6. In these embodiments, both a multi-functional dienophile and a multi-functional diene are added to the diene terminated multi-arm PIB co polymer described in detail above. Suitable multi-functional dienes include, but are not limited to, tris-furan, tetra-furan, penta-furan, hexa-furan, or other multifunctional furan, and combinations thereof. When these compounds react, the multi-functional multi-functional dienophiles will bond with both the multi-functional diene are the diene end groups on the multi-arm PIB co polymer, further cross linking the multi-arm PIB co polymers. See FIG. 5.

As set forth above, because the TPE is crosslinked using Diels-Alder retro-Diels-Alder chemistry, the crosslinking reaction is thermally reversible (by the retro-Diels-Alder reaction) at moderately elevated temperatures. The reversibility of the Diels-Alder retro-Diels-Alder reactions allows the recovery of the original components of the TPE and thus its recyclability and also gives the TPE the ability to be reshaped and reformed.

In light of the foregoing, it should be appreciated that the present invention significantly advances the art by providing a polyisobutylene-based thermoplastic elastomer that is structurally and functionally improved in a number of ways. While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

The following examples are offered to more fully illustrate the invention, but are not to be construed as limiting the scope thereof. Further, while some of examples may include conclusions about the way the invention may function, the inventor do not intend to be bound by those conclusions, but put them forth only as possible explanations. Moreover, unless noted by use of past tense, presentation of an example does not imply that an experiment or procedure was, or was not, conducted, or that results were, or were not actually obtained. Efforts have been made to ensure accuracy with respect to numbers used (e.g., amounts, temperature), but some experimental errors and deviations may be present. Unless indicated otherwise, parts are parts by weight, molecular weight is weight average molecular weight, temperature is in degrees Centigrade, and pressure is at or near atmospheric.

Example 1

This example concerns the synthesis of 3-(2-methoxyisopropyl)styrene (i) (MeOiPrSt), a novel monomer suitable for the subsequent preparation of novel graft copolymers carrying PIB arms fitted with furan end groups. The monomer was synthesized using the following reaction scheme:

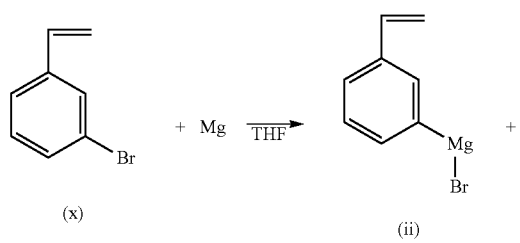

Figure 8:
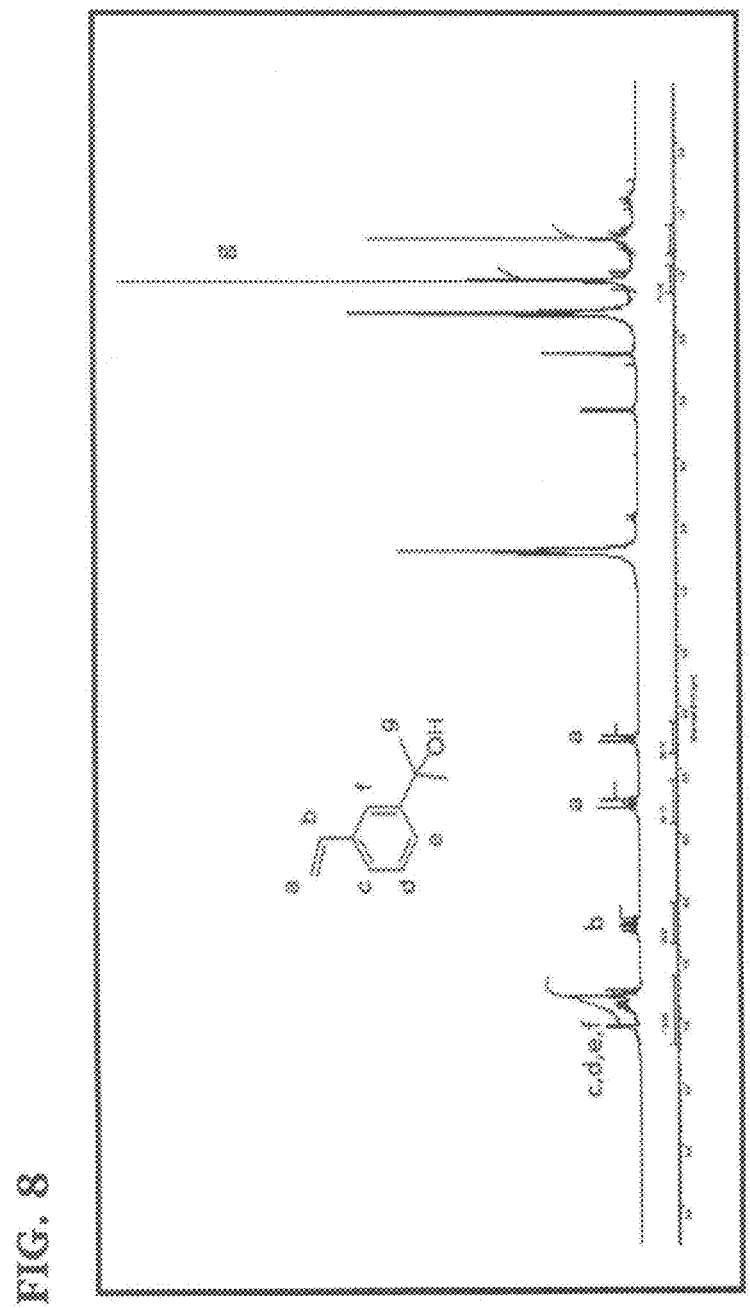
FIG. 8 is a $^1$H NMR spectrum of 3-(2-hydroxyisopropyl) styrene intermediary according to the method of at least one embodiment of the present invention.

A representative procedure for the synthesis of this monomer was as follows: In a 100 mL round bottom flask containing 25 g (0.137 mol) 3-bromostyrene (x) dissolved in dry THF was reacted with 13 g (0.535 mol) magnesium turning in THF at 15° C. for 4 hours under nitrogen atmosphere. Then 30 mL of acetone (xi) was added drop wise to this Grignard reagent (m-vinyl phenyl magnesium bromide) (ii) in 30 minutes at 0° C. and the mixture was stirred overnight at 25° C. The content of the flask was then poured into a beaker with 200 g ice and 5 g $NH_4Cl$. After extraction of the organic phase with diethyl ether three times, the solution was dried over anhydrous $MgSO_4$ overnight. The solids were filtered off and the solvents were removed under reduced pressure. The product was 3-(2-hydroxyisopropyl) styrene (iv) (96% conversion). FIG. 8 shows the 500 Mz proton NMR spectrum of the 3-(2-hydroxyisopropyl) styrene (iv). The product was used without purification for the preparation of the methoxy derivative (i).

Thus 22 g 3-(2-hydroxyisopropyl) styrene (iv) dissolved in 35 mL THF was added drop wise onto 6.4 g (0.27 mol) NaH in THF under a nitrogen atmosphere. The resulting mixture was stirred at 25° C. for 30 min. After drop wise adding 25 mL (0.40 mol) $CH_3I$ at 0° C., the solution was stirred overnight at 25° C., the NaI was then removed by filtration and the solvent was removed under reduced pressure to produce 3-(2-methoxyisopropyl) styrene monomer (i). Conversion was essentially quantitative as indicated by $^1H$ NMR spectroscopy (FIG. 2).

Example 2

This example concerns the preparation of a novel hexamer of 3-(2-methoxyisopropyl)styrene (HMeOiPrSt) by anionic polymerization.

The hexamerization of MeOiPrSt was conducted under high vacuum on a Schlenk line. This monomer was distilled over calcium hydride under reduced pressure and then distilled over dibutylmagnessium under high vacuum conditions just prior to anionic oligomerization. The reaction scheme below outlines the hexamerization. The hexa [3-(2-methoxyisopropyl) styrene] (HMeOiPrSt) was subsequently used to initiate the polymerization of isobutylene.

The hexa[3-(2-methoxyisopropyl)styrene (HMeOiPrSt) with an α-methylstyrene oligomer section and a sec-butyl head group was synthesized using the following reaction scheme:

Example 2a

An alternative method for the preparation of hexa[3-(methoxyisopropyl)styrene], and in general for the synthesis of oligomeric (10-16 mer) 3-(methoxyisopropyl)styrene, is by initiation with cumyl potassium, whose preparation is well known in anionic polymerization methodology. See Z. Huruska, G. Hurtrez, S. Walter, G. Riess, Polymer, 33, 11, 1992, the disclosure of which is hereby incorporated by reference in its entirety. This cumyl potassium initiator is prepared from cumyl methyl ether and sodium/potassium alloy of suitable composition. See F. Calderara, Z Huruska,

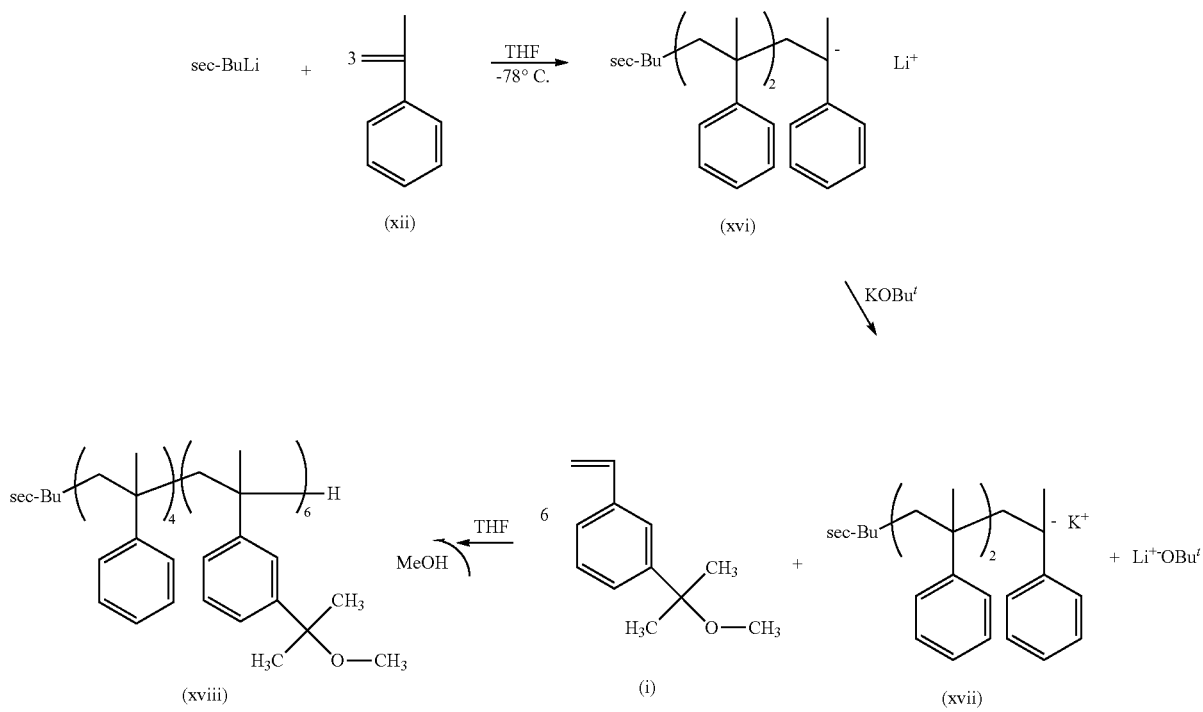

Thus, α-methylstyrene (xii) was distilled over calcium hydride under reduced pressure and then distilled over dibutylmagnessium under high vacuum. To 0.74 mL (5.70×10$^{-4}$ mol) α-methylstyrene (xii) in 40 mL THF was added drop wise 1.35 mL sec-BuLi (1.89×10$^{-3}$ mol) under strong stirring until the appearance of the characteristic red color. After the addition of 5.70 mL (1.0 M) KOBu$^t$ and 2.14 mL MeOiPrSt monomer (i) (1.14×10$^{-2}$ mol), oligomerization was conducted for 2 h, and terminated with methanol. The product was precipitated in excess methanol, filtered and dried under reduced pressure. The yield obtained was essentially quantitative.

Figure 9:
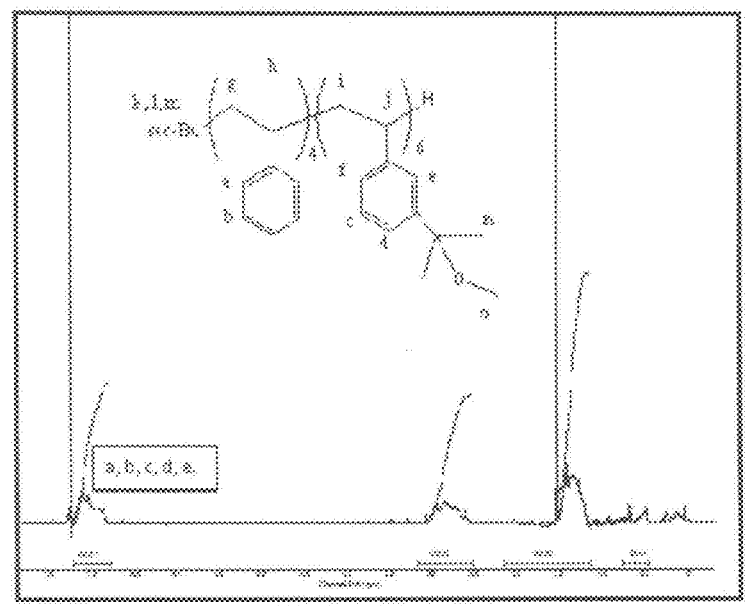
FIG. 9 $^1$H NMR spectrum of a sec-butyl-tetra(α-methylstyrene)-b-hexa[3-(methoxyisopropyl)styrene] according to at least one embodiment of the present invention.
Figure 10:
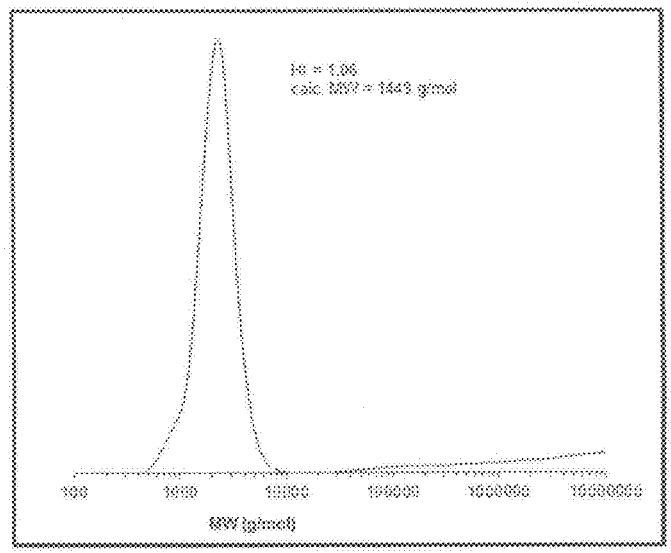
FIG. 10 is a gas permeation chromatography (GPC) trace of sec-butyl-tetra(α-methylstyrene)-b-hexa [3-(methoxyisopropyl)styrene] according to at least one embodiment of the present invention.

The structure of the product was analyzed by $^1$H NMR spectroscopy (see FIG. 9). The resonances in the $^1$H NMR spectrum indicate the aromatic, methine, methylene and methyl protons. FIG. 9. According to GPC analysis the molecular weight distribution (MWD) of the product was uniform and narrow ($M_w/M_n$=1.06) (See, FIG. 10).

G. Hurtrez, T. Nugay, G. Riess, Macromol Chem., 194, 1411, (1993), the disclosure of which is hereby incorporated by reference in its entirety. To a 300 mL round bottom flask having 100 mL freshly cryodistilled THF, previously prepared cumyl potassium is added drop wise under strong stirring until a slightly pink color persists (indication the absence of impurities). Then the required amount of cumyl potassium (5.7×10$^{-3}$ mol) and 1.14×10$^{-2}$ mol MeOiPrSt monomer are added, and the oligomerization is conducted for 30 min. at −78° C., The process is terminated with methanol, the product is precipitated in excess methanol, filtered and dried under reduced pressure, the product is obtained in essentially quantitative yield.

Example 3

This example concerns the preparation of a graft polymer with six PIB arms of $M_n$=4140 g/mol using the product prepared by the method described in Example 2. Termination of isobutylene polymerization with allyltrimethylsilane yielded allyl end groups at the PIB arm end. The general reaction scheme below shows these transformations.

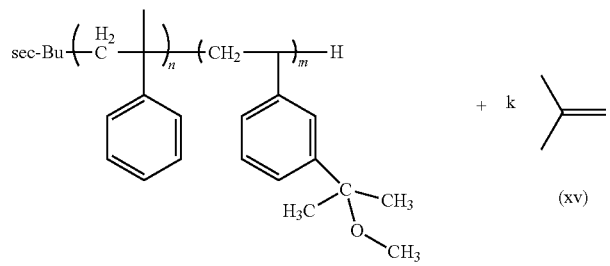

(v)

+ k [isobutylene]

(xv)

hexane/dichloromethane (60/40)
a) DBP
b) TiCl$_4$
c) allyltrimethylsilane

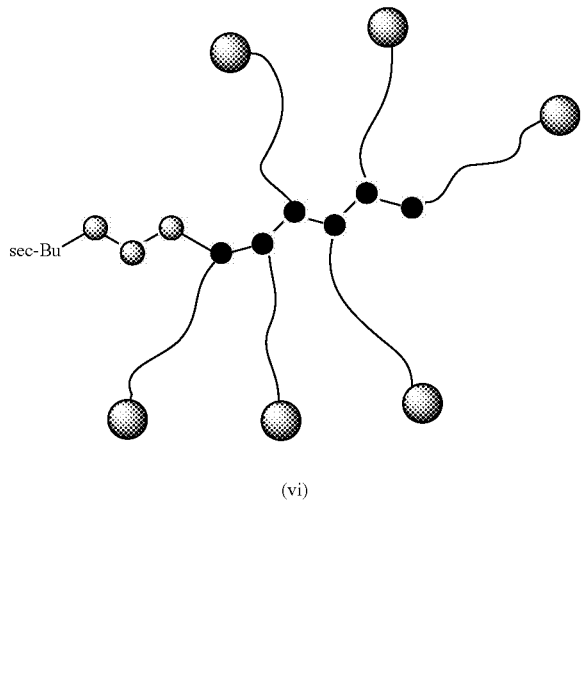

(vi)

● 3-(methoxyisopropyl)styrene

◯ α-methylstyrene

∽ PIB

◯ —CH$_2$-CH=CH$_2$

Figure 11:
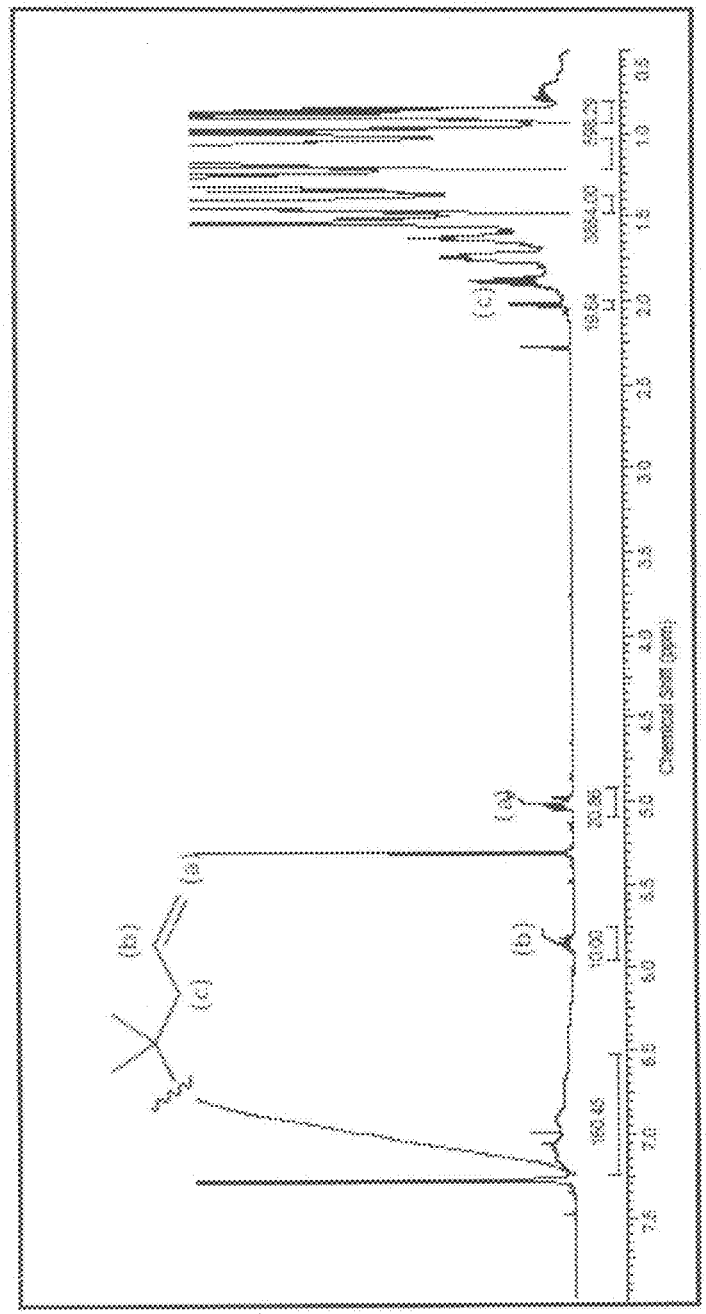
FIG. 11 is a $^1$H NMR spectrum of allyl terminated graft polymer according to the method of at least one embodiment of the present invention.
Figure 12:
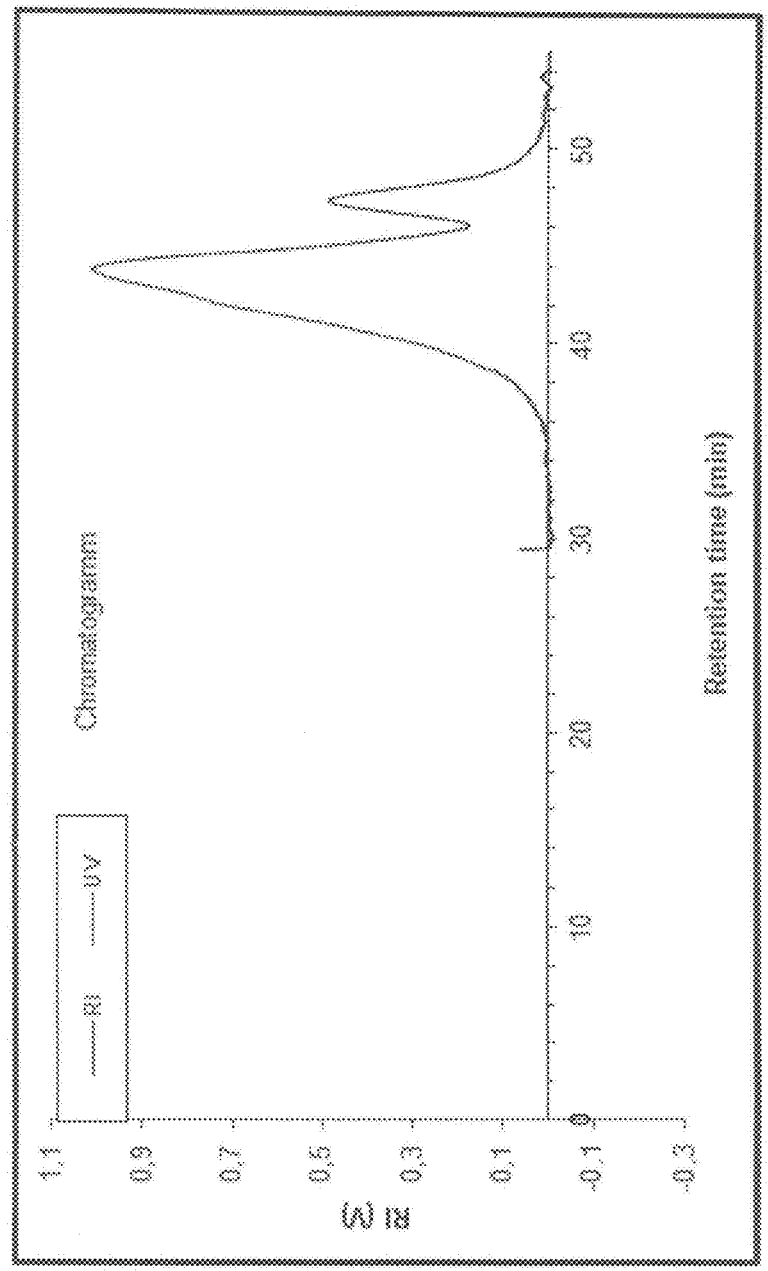
FIG. 12 is a GPC trace of allyl terminated graft polymer according to the method of at least one embodiment of the present invention.

The cationic polymerization was carried out under high vacuum/dry nitrogen system at −80° C. Into a 300 mL round bottom flask equipped with a magnetic stirrer was placed 60 mL dried and distilled hexane, 40 mL dried and distilled dichloromethane and 2.0×10$^{-4}$ mol of DTBP photoinitiator and cooled to −80° C. Under strong stirring 1.45×10$^{-3}$ mol of sec-butyl-tetra (α-methylstyrene)-b-hexa [3-(methoxyisopropyl) styrene] (v) initiator was added and the system stirred for 5 min. Then 1.07×10$^{-1}$ mol of isobutylene was added followed by the addition of 6.×10$^{-3}$ mol TiCl$_4$. The polymerization was allowed to proceed 60 min and was terminated with 4×10$^{-2}$ mol previously distilled and pre-chilled allyltrimethylsilane (ATM). After 30 min, the dichloromethane phase was removed under reduced pressure. The product was poured into 200 mL saturated NaHCO$_3$, the organic layer was separated, and the solvent was evaporated under reduced pressure. The product was dissolved in hexane and dried on MgSO$_4$ overnight. After filtration and evaporation of the solvent by rotavap, the polymer was dried in vacuo. The product (vi) was characterized by $^1$H NMR spectroscopy (FIG. 11) and GPC (FIG. 12). The observed resonances in the $^1$H NMR spectrum indicate the presence of allyl (5.10 and 5.85 ppm) end groups and methylene (2.00 ppm) protons of PIB. GPC showed the presence of two populations of molecular weights; average Mn=21344 g/mol with $M_w/M_n$=3.18. See FIG. 12.

Example 4

This example concerns the functionalization of the allyl end groups of grafted PIB arms (whose preparation is given in Example 3) by furan. The furan-functionalized graft polymer was synthesized using the reaction scheme shown in FIG. 12.

Figure 13:
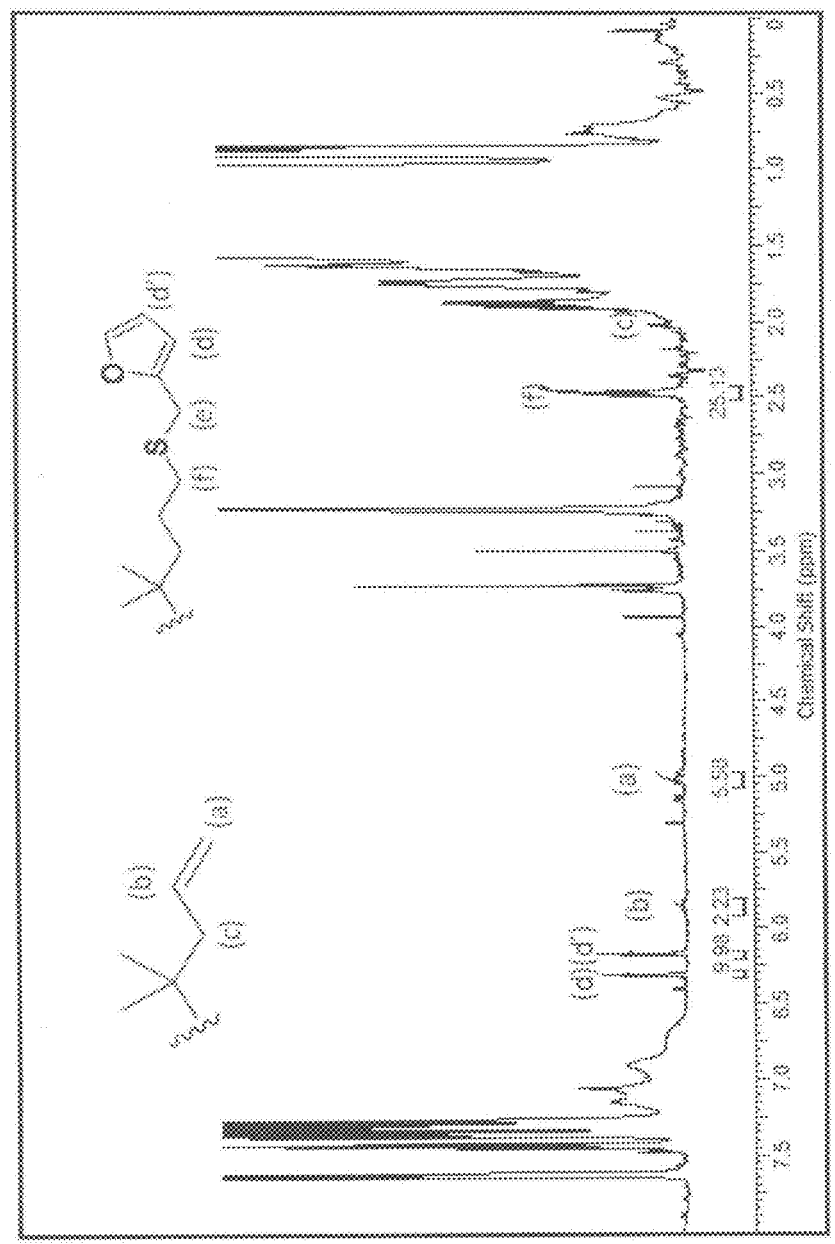
FIG. 13 is a $^1$H NMR spectrum of furan functionalized graft polymer according to at least one embodiment of the present invention.

A representative synthesis procedure is as follows: allyl terminated PIB(0.58 g, 2.75×10$^{-5}$ mol), 2,2-dimethoxy-2-phenyl acetophenone, DMPA photoinitiator (0.046 g, 1.78× 10$^{-4}$) and 10 ml CH$_2$Cl$_2$ were charged to a 50 mL glass round bottom flask under a nitrogen atmosphere. After dissolution, furfuryl mercaptan (0.054 mL, 5.4×10$^{-4}$ mol) was added and the system was mixed for 30 min. The sample was then irradiated using a medium pressure Hg lamp (Omnicure 2000S) for 60 min in an ice bath. The solvent was removed under reduced pressure and the crude reaction mixture was dissolved in hexane. The resulting solution was washed three times with methanol and placed under reduced pressure until constant weight was achieved. The product was characterized by NMR spectroscopy (FIG. 13). The new resonances associated with the furfuryl mercaptan moiety appeared at 6.20 and 6.30 ppm and 2.5 ppm.

Example 5

This Example concerns the crosslinking the furan-functionalized graft polymer (preparation of which is described in Example 4, above) by the DA reaction using a bismaleimide (BMI) to form the TPE of at least one embodiment of the present invention.

Figure 14:
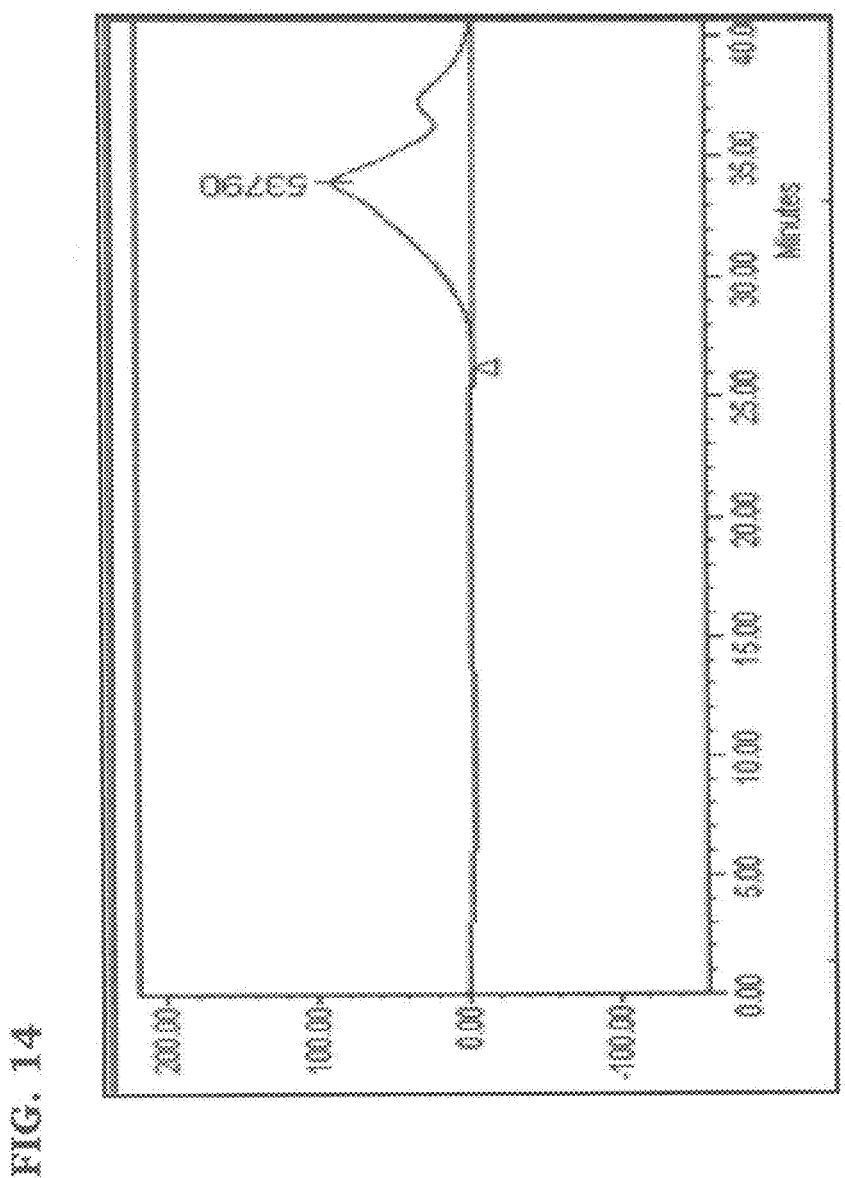
FIG. 14 is a GPC trace of Diels-Alder adduct according to at least one embodiment of the present invention after 2 days.

A representative procedure is as follows: furan-functionalized PIB (0.11 g, $5.2 \times 10^{-6}$ mol), BMI ($6.2 \times 10^{-3}$ g, $1.56 \times 10^{-5}$ mol) and 1 mL $CH_2Cl_2$ (or THF) were charged to a 20 mL glass vial under a nitrogen atmosphere. After dissolution, the system was mixed at RT for 2 days. No gelation (to indicate crosslinking) was observed. Then the bath temperature was raised to 45° C. After 2 days an aliquot was taken, the polymer was precipitated in methanol, dried and characterized by GPC (FIG. 14).

The shift of MW trace to lower retention times, corresponding to higher molecular weights (53,800 g/mol) than the initial one (21,300 g/mol), indicates the progress of the Diels-Alder reaction. See FIG. 14. At this stage elastic fibers were pulled from the system that exhibited elastic recovery. The use of UV radiation to accelerate the DA reaction seems to be a new method to accelerate adduct formation.

Example 6

This prophetic example illustrates that the network prepared in Example 5 may be rendered processable by heating to 120-150° C. and the PIB networks crosslinked by the DA reaction re-shaped at elevated temperatures.

In this example, a ~0.2 g sample of a solid PIB network (the preparation of which is described in Example 5, above) may be placed in a test tube, ~10 mL chlorobenzene solvent is added, and the system then heated to ~150° C. After heating for a short period of time, it is expected that the solid should dissolve, indicating that the network is processable at this temperature. Upon cooling the system to room temperature, it is expected that the will gel re-appear.

Example 7

Examples 7a and 7b are prophetic examples outlining alternative embodiments of the TPE of the present invention.

Example 7a

Figure 7:
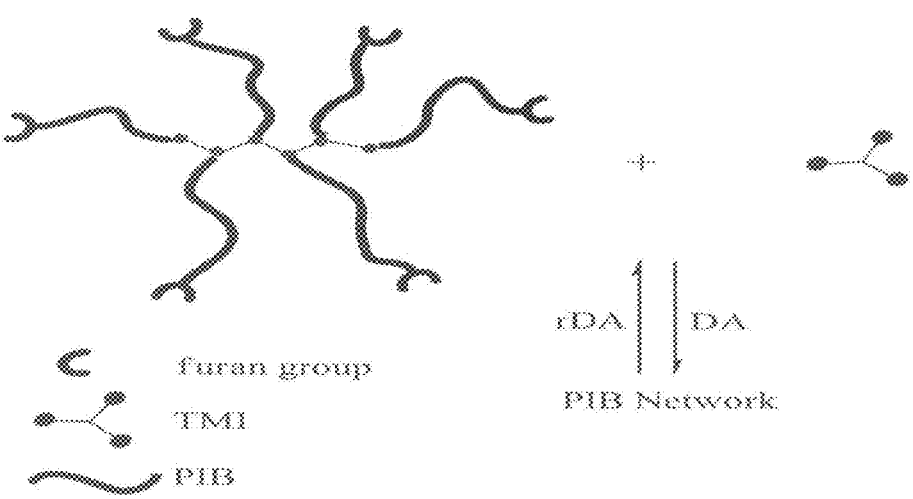
FIG. 7 is a sketch showing a strategy for forming a TPE network according to at least one embodiment of the present invention by reacting a diene (furan) terminated multi-arm PIB copolymer with multi-functional dienophiles (tris-maleimide) to form a TPE network according to at least one embodiment of the present invention.

This example concerns the synthesis of a PIB Network by crosslinking of the furan-functionalized graft (the preparation of which is described in Example 4, above) by the DA reaction using a trismaleimide (TMI) using the reaction scheme shown in FIG. 7.

A representative procedure is as follows: furan-functionalized PIB (0.11 g, $5.2 \times 10^{-6}$ mol), TMI ($6.8 \times 10^{-3}$ g, $1.30 \times 10^{-5}$ mol) and 1 mL $CH_2Cl_2$ (or THF) are charged to a 20 mL glass vial under a nitrogen atmosphere. After dissolution, the system is mixed at first at RT then at 45° C. To follow the progress of the DA reaction, aliquots are taken from the reaction mixture; the product is precipitated in methanol, dried and the solid product is characterized by GPC.

Example 7b

Another example concerns the conversion of the furan-functionalized graft (whose preparation is described in Example 4) to maleimide terminated graft by the DA reaction using a 10 fold excess of bis- or tris-maleimide. Subsequently, this product is used in a second DA reaction with the furan-functionalized graft polymer to obtain the PIB network. The synthesis of a PIB Network by two sequential Diels-Alder Reactions with BMI may be better understood with reference to FIG. 15. A similar network is obtained with TMI.

A representative procedure to implement this strategy is as follows Furan-functionalized PIB (0.11 g, $5.2 \times 10^{-6}$ mol), TMI ($6.8 \times 10^{-2}$ g, $1.30 \times 10^{-4}$ mol) and 2 ml $CH_2Cl_2$ (or THF) are charged to a 20 mL glass vial under a nitrogen atmosphere. After dissolution, the system is mixed first at RT then at 45° C. To follow the progress of the reaction, aliquots are taken from the reaction mixture, they are precipitated in methanol, dried, and they are characterized by GPC. After completion of the reaction, the excess TMI is removed by washing the product with hexane, the solvents are removed and dried in vacuum. The graft carrying TMI end groups is subsequently used in further DA reactions to crosslink furan-functionalized PIB (whose reparation is described in Example 4). The procedure is given in Example 7a.

Figure 15:
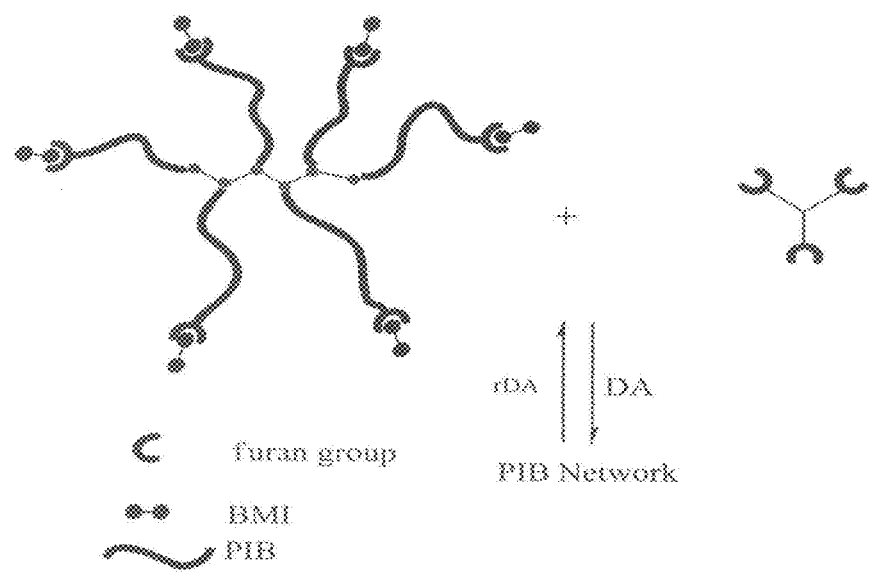
FIG. 15 is a sketch showing a strategy for forming a TPE network according to at least one embodiment of the present invention by reacting a diene (furan) terminated multi-arm PIB copolymer first with di-functional dienophiles (bis-maleimide) and then with multi-functional dienes (tris-furan) to form a TPE network according to at least one embodiment of the present invention.

This example concerns the DA functionalizing of furan-functionalized graft (whose preparation is described in Example 4) with a 10 fold excess of bis- or tris-maleimide, removing the excess unreacted bis- or tris-maleimide, and finally DA crosslinking the MI-functionalized graft with a tris-furan (TF) to PIB networks. FIG. 15 outlines this strategy.

The PIB networks may be prepared by two sequential DA Reactions according to the reaction scheme of FIG. 15 (only the second DA reaction is shown).

A representative procedure is as follows: Furan-functionalized PIB(0.11 g, $5.2 \times 10^{-6}$ mol), BMI ($6.2 \times 10^{-2}$ g, $1.56 \times 10^{-4}$ mol) (or TMI ($6.8 \times 10^{-2}$ g, $1.30 \times 10^{-4}$ mol)) and 2 ml $CH_2Cl_2$ (or THF) are charged to a 20 mL glass vial under a nitrogen atmosphere. After dissolution, the system is mixed first at RT then at 45° C. To follow the DA reaction, aliquots are removed from the reaction mixture during the reaction; the polymer is precipitated in methanol, dried and characterized by GPC. After completion of reaction, the excess BMI (or TMI) is removed by washing the product with hexane, the solvents are removed and the product is dried. Subsequently, the MI-functionalized product is crosslinked by a further DA reaction with TF, and a solid network is obtained.

What is claimed is:

1. A multi-arm polyisobutylene (PIB) polymer comprising:
   a) an oligomeric styrene pre-polymer having a sec-butyl head group, a poly(α-methylstyrene) segment from 3 to 5 units in length and a poly[3-(2-methoxyisopropyl)styrene] segment from 3 units to 50 units in length and having the structure of formula (v):

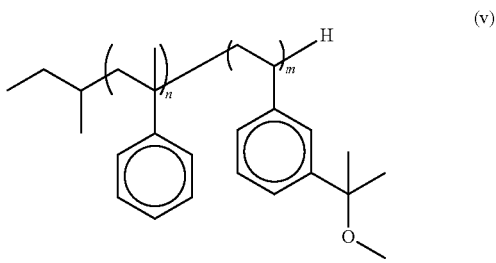

wherein n is an integer from 3 to 5 and m is an integer from 3 to 50; and b) at least one PIB arm extending from each 3-(2-methoxyisopropyl)styrene wherein said PIB arms are terminated with end groups selected from the group consisting of allyls, dienes, and furans.

2. The multi-arm PIB polymer of claim 1 wherein said end groups are allyl end groups.

3. The multi-arm PIB polymer claim 2 having the formula (vi):

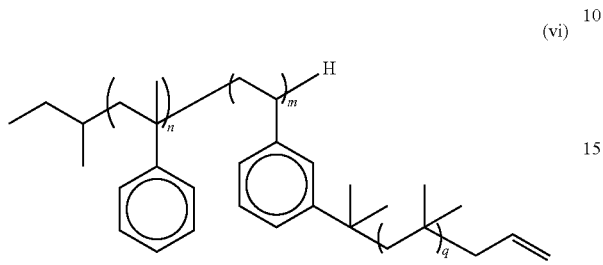

(vi)

wherein n is an integer from 3 to about 5, m is an integer from 3 to 50, and q is an integer from 10 to 10,000.

4. The multi-arm PIB polymer of claim 1 wherein said end groups are diene end groups.

5. The multi-arm PIB polymer of claim 1 wherein said end groups are furan end groups.

6. The multi-arm PIB polymer of claim 5 having the formula (vii):

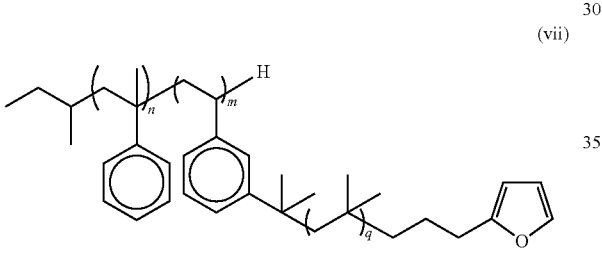

(vii)

wherein n is an integer from 2 to 5, m is an integer from 3 to 50, and q is an integer from 10 to 10,000.

7. A method for making a thermoplastic elastomer network comprising reacting: the multi-arm polyisobutylene polymer of claim 1; a plurality of multi-functional dienophiles; and a plurality of tris-furan molecules to form a reversibly crosslinked thermoplastic elastomer.

8. A method for synthesizing a multi-arm polyisobutylene having an oligomeric styrene, a sec-butyl head group, and allyl end groups comprising:
a) reacting a sec-butyl lithium and an α-methylstyrene to form an α-methylstyrene oligomer of from 3 units to 5 units in length, said α-methylstyrene oligomer having a sec-butyl head group and a lithium ion;
b) reacting the α-methylstyrene oligomer of step (a) with potassium tert-butoxide to replace the lithium ion on the α-methylstyrene oligomer with a potassium ion;
c) reacting the methylstyrene oligomer of step (b) with a 3-(2-methoxyisopropyl)styrene to form an oligomeric styrene pre-polymer having a sec-butyl head group, a poly(α-methylstyrene) segment of from 3 to 5 units in length, and a poly[3-(2-methoxyisopropyl)styrene] segment of from 3 to 50 units in length;
d) combining the oligomeric styrene pre-polymer of step (c), a stoichiometric excess of isobutylene, and a photoinitiator, wherein said isobutylene is added to at least one of the 3-(2-methoxyisopropyl)styrene units of said poly[3-(2-methoxyisopropyl)styrene] segment of said oligomeric styrene pre-polymer by cationic polymerization to create PIB arms of from 10 units to 10,000 units in length extending from each of said 3-(2-methoxyisopropyl)styrene units; and
e) adding allyltrimethylsilane to terminate the isobutylene polymerization and place an allyl end group on the end of said PIB arms.

9. A method for synthesizing a multi-arm polyisobutylene having an oligomeric styrene, a sec-butyl head group, and diene end groups comprising:
a) dissolving the allyl-terminated multi-arm polyisobutylene of claim 3 and a photoinitiator in a solvent to provide a solution;
b) adding furfuryl mercaptan to provide a solution comprising furfuryl mercaptan and the solution of step (a);
c) irradiating the solution of step (b); and
d) removing the solvent to provide a multi-arm polyisobutylene having an oligomeric styrene, a sec-butyl head group, and diene end groups.

10. The method of claim 9 further comprising the steps of:
e) redissolving the multi-arm polyisobutylene having an oligomeric styrene, a sec-butyl head group, and a diene end groups of step (d) in hexane;
f) washing the solution of step (e) with methanol; and
g) removing said hexane and said methanol under reduced pressure to leave the multi-arm polyisobutylene having an oligomeric styrene, a sec-butyl head group, and a diene end groups.

11. The method of claim 9 wherein the photoinitiator is 2,2-dimethoxy-2-phenyl acetophenone and the solvent is dichloromethane.

12. A method for making a thermoplastic elastomer network comprising reacting the multi-arm polyisobutylene having an oligomeric styrene, a sec-butyl head group, and a diene end groups of claim 9 and a plurality of multi-functional dienophiles to form a reversibly crosslinked thermoplastic elastomer.

13. The method of claim 12, wherein said diene end groups are a furan end groups.

14. The method of claim 12, wherein said multi-functional dienophiles are selected from the group consisting of aliphatic/aromatic bis-maleimide, tris-maleimide, and combinations thereof.

* * * * *